US012285478B2

(12) United States Patent
Dominowski et al.

(10) Patent No.: US 12,285,478 B2
(45) Date of Patent: *Apr. 29, 2025

(54) FOOT-AND-MOUTH DISEASE VACCINE

(71) Applicants: Zoetis Services LLC, Parsippany, NJ (US); United States of America, as Represented by the Secretary of Agriculture, Washington, DC (US)

(72) Inventors: Paul Joseph Dominowski, Kalamazoo, MI (US); John Morgan Hardham, Kalamazoo, MI (US); James Alan Jackson, Kalamazoo, MI (US); Cyril Gerard Gay, Bethesda, MD (US); Luis Leandro Rodriguez, Niantic, CT (US); Peter William Krug, East Setauket, NY (US); Aida Elizabeth Rieder, Westbrook, CT (US)

(73) Assignees: Zoetis Services LLC, Parsippany, NJ (US); United States of America, as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,123

(22) Filed: Nov. 16, 2023

(65) Prior Publication Data

US 2024/0197855 A1    Jun. 20, 2024

Related U.S. Application Data

(63) Continuation of application No. 17/180,223, filed on Feb. 19, 2021, now Pat. No. 11,865,171, which is a continuation of application No. 16/374,105, filed on Apr. 3, 2019, now Pat. No. 10,967,058, which is a continuation of application No. 15/543,630, filed as application No. PCT/US2016/013587 on Jan. 15, 2016, now Pat. No. 10,478,487.

(60) Provisional application No. 62/104,314, filed on Jan. 16, 2015.

(51) Int. Cl.
 *A61K 39/135* (2006.01)
 *A61K 39/00* (2006.01)
 *A61K 39/12* (2006.01)
 *A61K 39/39* (2006.01)

(52) U.S. Cl.
 CPC ............ *A61K 39/135* (2013.01); *A61K 39/12* (2013.01); *A61K 39/39* (2013.01); *A61K 2039/5252* (2013.01); *A61K 2039/552* (2013.01); *A61K 2039/555* (2013.01); *A61K 2039/55505* (2013.01); *A61K 2039/55511* (2013.01); *A61K 2039/55561* (2013.01); *A61K 2039/55566* (2013.01); *A61K 2039/55583* (2013.01); *C12N 2770/32034* (2013.01); *C12N 2770/32134* (2013.01)

(58) Field of Classification Search
 None
 See application file for complete search history.

(56) References Cited

U.S. PATENT DOCUMENTS

| 4,471,054 | A | 9/1984 | Lattore et al. | |
| 4,732,971 | A | 3/1988 | DiMarchi | |
| 10,117,921 | B2 | 11/2018 | Dominowski | |
| 10,478,487 | B2 * | 11/2019 | Dominowski | ....... A61K 39/135 |
| 10,967,058 | B2 * | 4/2021 | Dominowski | ......... A61K 39/12 |
| 11,865,171 | B2 * | 1/2024 | Dominowski | ......... A61K 39/39 |
| 2005/0118701 | A1 | 6/2005 | Zhou | |
| 2005/0220814 | A1 | 10/2005 | Dominowski | |
| 2008/0038295 | A1 | 2/2008 | Baker, Jr. | |
| 2009/0324641 | A1 | 12/2009 | Dominowski | |
| 2011/0014232 | A1 | 1/2011 | Maree | |
| 2011/0129494 | A1 | 6/2011 | Detraz | |
| 2012/0315295 | A1 | 12/2012 | Rieder | |
| 2013/0084306 | A1 * | 4/2013 | Davis | .................. A61K 39/099 424/193.1 |
| 2020/0078456 | A1 | 3/2020 | Dominowski | |

FOREIGN PATENT DOCUMENTS

WO    WO 2007/095316    *    8/2007

OTHER PUBLICATIONS

Valarcher, J.-F., et al., "Incursions of Foot-and-Mouth Disease Virus into Europe between 1985 and 2006," Journal Compilation © 2008 Blackwell Verlag • Transboundary and Emerging Diseases. 55 (2008), pp. 14-34.
Perez, Andres M., et al., "Variation in the VP1 gene of Foot-and-mouth disease virus serotype A associated with epidemiological characteristics of outbreaks in the 2001 epizootic in Argentina," J. Vet. Diagn. Invest. 20: pp. 433-439 (2008).
Perez, Andres M., et al., "Control of a foot-and-mouth disease epidemic in Argentina," Preventive Veterinary Medicine 65 (2004) pp. 217-226.
Stram, Yehuda, et al., "Nucleotide Sequence of the PI Region of Serotype Asia I Foot-and-Mouth Disease Virus," Virus Genes 8:3, pp. 275-278, 1994.
Carrillo, C., et al., "Comparative Genomics of Foot-and-Mouth Disease Virus†," Journal of Virology, May 2005, pp. 6487-6504.
Pereda, A.J., et al., "Full length nucleotide sequence of foot-and-mouth disease virus strain O1 Campos/Bra/58," Arch Virol (2002) 147: pp. 2225-2230.
Ren et al. (Vaccine. 201; 29: 7960-7965).

(Continued)

*Primary Examiner* — Shanon A. Foley
(74) *Attorney, Agent, or Firm* — Vyacheslav Vasilyev

(57) ABSTRACT

Compositions for prevention of Foot and Mouth Disease (FMD) are provided, comprising an antigen component in the amount equivalent to 0.5-20 μg FMD virus and an adjuvant component comprising oil, an immunostimulatory oligonucleotide, and a polycationic carrier. Methods of using the composition, as well as the methods of reducing FMD persistence are also provided.

13 Claims, 1 Drawing Sheet
Specification includes a Sequence Listing.

(56) References Cited

OTHER PUBLICATIONS

Instant SEQ ID No. 8 alignment with Geneseq access No. ARW70773 by Debelak et al. in WO 2008068638 Jun. 2008.
Stills Jr. (ILAR Journal; 2005; 46(3): 280-293).
Soren Alexandersen "Aspects of the persistence of foot-and-mouth disease virus in animals—the carrier problem," Microbes and Infection 4 (2002), pp. 1099-1110.
P. Moonen "Carriers of foot-and-mouth disease virus: A Review," Veterinary Quarterly, (2000), 22:4, pp. 193-197.
Sabena Uddowla, et al., "A Safe Foot-and-Mouth Disease Vaccine Platform with Two Negative Markers for Differentiating Infected from Vaccinated Animals," Journal of Virology, Nov. 2012 vol. 86, No. 21, pp. 11675-11685.
Paul Lawrence, et al., "Foot-and-mouth disease virus (FMDV) with a stable FLAG epitope in the VP1 G-H loop as a new tool for studying FMDV pathogenesis," Virology 436 (2013), pp. 150-161.

* cited by examiner

| Lane | Sample |
|---|---|
| 1 | Marker |
| 2 | Pre-10 micron filter pellet |
| 3 | Pre-10 micron filter sup |
| 4 | Post-10 micron filter |
| 5 | Post-4.5 micron filter |
| 6 | Post-.8/.2 micron filter |
| 7 | One hour post-BEI w/ thio |
| 8 | Vaccine Batch #3 |
| 9 | BEI/Vacc Peg Fract #10 |
| 10 | A24 Control |
| 11 | A24 Control (1:10) |

← anti FMDV-3D Mab F19-59

← anti FMDV-VP1 Mab 6HC4

SEQUENCE LISTING

```
Sequence total quantity: 30
SEQ ID NO: 1            moltype = DNA  length = 23
FEATURE                 Location/Qualifiers
misc_feature            1..23
                        note = CpG oligonucleotide
source                  1..23
                        mol_type = other DNA
                        organism = synthetic construct
SEQUENCE: 1
tcgtcgacga tcggcgcgcg ccg                                           23

SEQ ID NO: 2            moltype = DNA  length = 23
FEATURE                 Location/Qualifiers
misc_feature            1..23
                        note = CpG oligonucleotide
source                  1..23
                        mol_type = other DNA
                        organism = synthetic construct
SEQUENCE: 2
tcgacgtcga tcggcgcgcg ccg                                           23

SEQ ID NO: 3            moltype = DNA  length = 24
FEATURE                 Location/Qualifiers
misc_feature            1..24
                        note = CpG oligonucleotide
source                  1..24
                        mol_type = other DNA
                        organism = synthetic construct
SEQUENCE: 3
tcgacgtcga tcggcgcgcg ccgt                                          24

SEQ ID NO: 4            moltype = DNA  length = 23
FEATURE                 Location/Qualifiers
misc_feature            1..23
                        note = CpG oligonucleotide
misc_feature            1
                        note = 5'-Iodo-2'-deoxyuridine
source                  1..23
                        mol_type = other DNA
                        organism = synthetic construct
SEQUENCE: 4
ncgacgtcga tcggcgcgcg ccg                                           23

SEQ ID NO: 5            moltype = DNA  length = 24
FEATURE                 Location/Qualifiers
misc_feature            1..24
                        note = CpG oligonucleotide
misc_feature            1
                        note = 5'-Iodo-2'-deoxyuridine
source                  1..24
                        mol_type = other DNA
                        organism = synthetic construct
SEQUENCE: 5
ncgacgtcga tcggcgcgcg ccgt                                          24

SEQ ID NO: 6            moltype = DNA  length = 24
FEATURE                 Location/Qualifiers
misc_feature            1..24
                        note = CpG oligonucleotide
misc_feature            1
                        note = 5'-Iodo-2'-deoxyuridine
source                  1..24
                        mol_type = other DNA
                        organism = synthetic construct
SEQUENCE: 6
ncgacgtcga tcggcgcgcg ccgt                                          24

SEQ ID NO: 7            moltype = DNA  length = 23
FEATURE                 Location/Qualifiers
misc_feature            1..23
                        note = CpG oligonucleotide
misc_feature            1
                        note = 5'-Ethyl-2'-deoxyuridine
source                  1..23
                        mol_type = other DNA
                        organism = synthetic construct
SEQUENCE: 7
ncgacgtcga tcggcgcgcg ccg                                           23
```

```
SEQ ID NO: 8           moltype = DNA   length = 24
FEATURE                Location/Qualifiers
misc_feature           1..24
                       note = CpG oligonucleotide
misc_feature           1
                       note = 5'-Iodo-2'-deoxyuridine
source                 1..24
                       mol_type = other DNA
                       organism = synthetic construct
SEQUENCE: 8
ncgtcgacga tcggcggccg ccgt                                            24

SEQ ID NO: 9           moltype = DNA   length = 24
FEATURE                Location/Qualifiers
misc_feature           1..24
                       note = CpG oligonucleotide
misc_feature           1
                       note = 5'-Iodo-2'-deoxyuridine
source                 1..24
                       mol_type = other DNA
                       organism = synthetic construct
SEQUENCE: 9
ncgtcgacga tcggcggccg ccgt                                            24

SEQ ID NO: 10          moltype = DNA   length = 23
FEATURE                Location/Qualifiers
misc_feature           1..23
                       note = CpG oligonucleotide
source                 1..23
                       mol_type = other DNA
                       organism = synthetic construct
SEQUENCE: 10
tcgtcgacga tcggcgcgcg ccg                                             23

SEQ ID NO: 11          moltype = DNA   length = 20
FEATURE                Location/Qualifiers
misc_feature           1..20
                       note = RNA
source                 1..20
                       mol_type = other DNA
                       organism = synthetic construct
SEQUENCE: 11
ttgttgttgt tgttgttgtt                                                 20

SEQ ID NO: 12          moltype = DNA   length = 20
FEATURE                Location/Qualifiers
misc_feature           1..20
                       note = RNA
source                 1..20
                       mol_type = other DNA
                       organism = synthetic construct
SEQUENCE: 12
ttattattat tattattatt                                                 20

SEQ ID NO: 13          moltype = DNA   length = 19
FEATURE                Location/Qualifiers
misc_feature           1..19
                       note = RNA
source                 1..19
                       mol_type = other DNA
                       organism = synthetic construct
SEQUENCE: 13
aaacgctcag ccaaagcag                                                  19

SEQ ID NO: 14          moltype = DNA   length = 21
FEATURE                Location/Qualifiers
misc_feature           1..21
                       note = DNA/RNA
misc_feature           11..17
                       note = ribonucleotides
source                 1..21
                       mol_type = other DNA
                       organism = synthetic construct
SEQUENCE: 14
tcgtcgtttt gttgtgtttt t                                               21

SEQ ID NO: 15          moltype = DNA   length = 10867
FEATURE                Location/Qualifiers
```

| misc_feature | 1..10867 |
| --- | --- |
| | note = Fusion nucleotide: Foot and Mouth Disease Virus |
| | (FMDV) and Bovine Rhinovirus Type 2 (BRV2) |
| source | 1..10867 |
| | mol_type = other DNA |
| | organism = synthetic construct |

SEQUENCE: 15

```
ggggccggcc aatccagtcc ggcgaccggc tcgcagaacc aatctggcaa cactggcagc    60
ataattaaca actactacat gcagcaatac cagaactcca tggcacacac gttgggagac   120
aatgccatca gtggaggctc caacgagggc tccacggaca caacttcaac acacacaacc   180
aacactcaaa acaatgactg gttctcgaag ctcgccagtt cagcttttac cggtctgttc   240
ggtgcactgc tcgccgacaa gaagacagag gaaacgacac ttcttgagga ccgcatcctc   300
accacccgca acgggcacac cacctcgacg acccaatcga gtgtgggtgt cacacacggg   360
tactccacag aggaggacca cgttgctggg cccaacacat cgggcctgga gacgcgagtg   420
gtgcaggcag agagattcta caaaaagtac ttgtttgact ggacaacgga caaggcattt   480
ggacacctgg aaaagctgga gctcccgtcc gaccaccacg gtgtctttgg acacttggtg   540
gactcgtacg cctatatgag aaatggctgg gatgttgagg tgtccgctgt tggcaaccag   600
ttcaacggcg ggtgcctcct ggtggccatg gtacctgaat ggaaggaatt tgacacgggg   660
gagaaatacc aactcaccct tttcccgcac cagtttatta gcccagaac taacatgact   720
gcccacatca cggtcccccta ccttggtgtg aacaggtatg atcagtacaa gaagcataag   780
ccctggacat tggttgtcat ggtcgtgtcg ccacttacgg tcaacaacac tagtgcggca   840
caaatcaagg tctacgccaa catagctccg acctatgtc acgtggccgg tgaactcccc   900
tcgaaagagg ggatttttcc ggttgcatgt gcggacggtt acggaggatt ggtgacgaca   960
gacccgaaga cagctgaccc tgcttatggc aaggtgtaca acccgcctag gactaactac  1020
cctgggcgct tcaccaacct gttggacgtg gccgaagcgt gtcccacttt cctctgcttt  1080
gacgacggga aacgtacgt caccacgcgg acggatgaca cccgacttt ggccaagttt  1140
gacctttccc ttgccgcaaa acatatgtcc aacacatacc tgtcaggat gctcagtac  1200
tacacacagt actctggcac catcaatttg catttcatgt tcacaggttc cactgattca  1260
aaggcccgat acatggtggc ctacatccca cctggggtgg agacaccacc ggacacacct  1320
gaaagggctg cccactgcat tcacgctgaa tgggacacta gctaaactc caaattcact  1380
ttctcaatcc cgtacgtatc cgccgcggat tacgcgtaca cagcgtctga cacggcagaa  1440
acaatcaacg tacaggatg gtctgcatc taccaaatta cacacgggaa ggctgaaaat  1500
gacaccttgg tcgtgtcggt tagcgccggc aaagactttg agttgcgcct cccgattgac  1560
ccccgccagc agaccaccgc taccgggaa tcagcagacc cggtcaccac caccgtgag  1620
aactacggcg gtgagacaca atccagaga cgtcaccaca cggacattgg ttttcatcatg  1680
gacagatttg tgaagatcca aagcttgagc ccaacacatg tcattgacct catgcagact  1740
caccaacacg gtctggtggg tgccttgctg cgtgcagcca cgtactactt ttctgacctg  1800
gaaattgttg acggcacga aggcaatctg acctgggtgc caacggcgc ccctgaatca  1860
gccctgttga acaccagcaa cccactgcc tacaacaagg tgccattcac gagactcgct  1920
ctcccctaca ctgcgccgca ccgtgtgctg gcaacagtgt acaacgggac gagtaagtat  1980
gctgtgggtg gttcaggcag aagaggcgac atggggtctc tcgcggcgcg agtcgtgaaa  2040
cagcttcctg cttcatttaa ctacggtgca atcaaggccg acgccatcca cgaacttctc  2100
gtgcgcatga aacgggccga gctctactgc cccagaccgc tgttggcaat agaggtgtct  2160
tcgcaagaca ggcacaagca aaagatcatt gcaccagcaa agcagcttct gaattttgac  2220
ctgcttaagc tagccggaga cgttgagtcc aaccctgggc ccttcttctt ctccgacgtt  2280
aggtcaaact tttccaagct ggtagacaca atcaaccaga tgcaggaaga catgtccaca  2340
aagcacggac ctgactttaa ccggttggtg tccgcttttg aggagttgac cactggagtg  2400
aaagccatca ggaccggtct tgacgaggcc aagcccggt acaagcttat caagctcctg  2460
agccgcctgt cgtgcatggc cgctgtggca gcacggtcaa aggacccagt ccttgtggcc  2520
atcatgctgc ctgacaccgg tctcgagatt ctggacagca ccttcgtcgt gaagaagatc  2580
tccgactcgc tctccagtct cttccacgtg ccggccccc tcttcagttt cggagcccg  2640
attctgttag ccgggttggt caaggtcgcc tcgagtttct tccggtccac gcccgaagac  2700
cttgagagag cagagaaaca gctcaaagca cgtgacatca acgacatttt cgccattctc  2760
aagaacggcg agtggctggt caaattgatc cttgccatcc gcgactggat caaggcatgg  2820
atagcctcag aagaaaagtt tgtcaccacg acagacttgg tacctagcat ccttgaaaaa  2880
cagcaggacc tcaacgaccc aagcaagtac aaggaagcca aggagtggct cgacaacgcg  2940
cgccaagcgt gtttgaagag cgggaacgtc cacattgcca acctgtgcaa agtggtcgcc  3000
ccggcaccca gcaggtcgag acccgagccc gtggtcgtt gcctccgtgg caagtccggt  3060
cagggcaaga gtttccttgc aaacgtgctc gcacaagcaa tctctaccca tttcactggc  3120
aggaccgatt cagtttggta ctgcccgcct gaccctgacc acttcgacgg ttacaaccaa  3180
cagactgtcg ttgtgatgga cgatttgggc cagaacccg acggcaaaga cttcaagtac  3240
ttcgcccaaa tggtttcaac aacggggttc atcccgccca tggcatcgct tgaggataaa  3300
ggcaaacccct tcaacagtaa ggtcatcata gcaaccacca cctgtactc gggcttcacc  3360
ccgaggacta tggtgtgccc tgatgccctg acccggaggt ttcactttga catcgacgtt  3420
agcgccaagg acgggtacaa aattaacaac aaattgacaa tcatcaaagc acttgaagat  3480
actcacacca acccagtggc aatgtttcag tacgactgtg cccttctcaa cggcatggct  3540
gttgaaatga gagaatgcat acaagatatg ttcaagcctc aaccacccct tcagaacgtg  3600
taccaactgg ttcaagaggt gattgagcgg gtggagctca acgagaaggt gtcgagccac  3660
ccgatttctca aacagactc aattccttcc caaaaatccg tgttgtactt cctcattgag  3720
aaaggacagc acgaggcagc aattgaattc tttgagggca tggtgcacga ctccatcaag  3780
gaggagctcc ggccgctcat ccaacaaacc tcatttgtga aacgcgcttt taagcgcctg  3840
aaggaaaact ttgagattgt tgcccctatgt ctgaccctcc tggccaacat agtgatcatg  3900
atccgcgaaa ctcgcaagag acagaagatg gtggacgatg cagtgagtga gtacattgag  3960
agagcaacca ccaacgacga cgaaagact cttgatggga ggaaaagaa ccctctgaa  4020
accagcggtg ccagcaccgt cggcttcaga gagagacctc tcccaggca aaaggcgcgt  4080
aatgacgaga actccgagcc cgcccagcct gctgaagage aaccacaagc tgaaggacccc  4140
tacgctggcc cgatggagag accagttaaa gttaaagtga agcaaaagc cccggtcgtt  4200
aaggaaggac cttacgaggg accggtgaag aagcctgttg ctttgaaagt gaaagctaag  4260
aacttgatcg tcactgagag tggtgcccca ccgaccgact tgcaaaagtt ggtcatgggc  4320
```

```
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag gacaggacat gctctcagac gctgcgctca ggggccggcc aatccagtcc    4560
ggcgaccggc tcgcagaacc aatctggcaa cactggcagc ataattaaca actactacat    4620
gcagcaatac cagaactcca tggacacaca gttgggagac aatgccatca gtggaggctc    4680
caacgagggc tccacggaca caacttcaac acacacaacc aacactcaaa caatgactg     4740
gttctcgaag ctcgccagtt cagcttttac cggtctgttc ggtgcactgc tcgccgacaa    4800
gaagacagag gaaacgacac ttcttgagga ccgcatcctc accacccgca acgggcacac    4860
cacctcgacg acccaatcga gtgtgggtgt cacacacggg tactccacag aggaggacca    4920
cgttgctggg cccaacacat cgggcctgga gacgcgagtg gtgcaggcag agagattcta    4980
caaaaagtac ttgtttgact ggacaacgga caaggcattt ggacacctgg aaaagctgga    5040
gctcccgtcc gaccaccacg gtgtctttgg acacttggtg gactcgtacg cctatatgag    5100
aaatggctgg gatgttgagg tgtccgctgt tggcaaccag ttcaacggcg ggtgcctcct    5160
ggtggccatg gtacctgaat ggaaggaatt tgacacacgg gagaaatacc aactcaccct    5220
tttcccgcac cagtttatta gccccagaac taacatgact gcccacatca cggtcccta    5280
ccttggtgtg aacaggtatg atcagtacaa gaagcataag ccctgacat tggttgtcat    5340
ggtcgtgtcg ccacttacgg tcaacaacac tagtgcggca caaatcaagg tctacgccaa    5400
catagctccg acctatgttc acgtggccgg tgaactcccc tcgaaagagg ggattttccc    5460
ggttgcatgt gcggacggtt acggaggatt ggtgacgaca gacccgaaga cagctgaccc    5520
tgcttatggc aaggtgtaca acccgcctag gactaactac cctgggcgct tcaccaacct    5580
gttgacgtg gccgaagcgt ctcccacttt cctctgcttt gacgacggga aaccgtacgt    5640
caccacgcgg acgatgaca cccgactttt ggccaagttt gacctttccc ttgccgcaaa    5700
acatatgtcc aacacatacc tgtcaggat tgctcagtac tacacacagt actctggcac    5760
catcaatttg catttcatgt tcacaggttc cactgattca aaggcccgat acatggtggc    5820
ctacatccca cctggggtgg agacaccacc ggacacacct gaaagggctg cccactgcat    5880
tcacgctgaa tgggacactg gactaaactc caaattcact ttctcaatcc cgtacgtatc    5940
cgccgcggat tacgcgtaca cagcgtctga cacggcagaa acaatcaacg tacagggatg    6000
ggtctgcatc taccaaatta cacacgggaa ggctgaaaat gacaccttgg tcgtgtcggt    6060
tagcgccggc aaagactttg agttgcgcct cccgattgac ccccgccaag agaccaccgc    6120
taccggggaa tcagcagacc cggtcaccac caccgtggag aactacgcg gtgagacaca     6180
aatccagaga cgtcaccaca cggacattgg tttcatcatg gacagatttg tgaagatcca    6240
aagcttgagc ccaacacatg tcattgacct catgcagact caccaacacg gtctggtggg    6300
tgccttgctg cgtcgagcca cgtactactt ttctgacctg gaaattgttg tacggccaga    6360
aggcaatctg acctgggtgc ccaacgcgc ccctgaatca gccctgttga acaccagcaa     6420
ccccactgcc tacaacaagg caccattcac gagactcgct ctcccctaca ctgccgcgca    6480
ccgtgtgctg gcaacagtgt acaacgggac gagtaagtat gctgtgggtg gttcaggcag    6540
aagaggcgac atgggtctc tcgcggcgcg agtcgtgaaa cagcttcctg cttcatttaa     6600
ctacgttgca atcaaggccg acgccatcca cgaacttctc gtgcgcatga acgggccga    6660
gctctactgc cccagaccgc tgttggcaat agaggtgtct tcgcaagaca ggcacaagca    6720
aaagatcatt gcaccagcaa agcagcttct gaattttgac ctgcttaagc tagccggaga    6780
cgttgagtcc aaccctgggc ccttcttctt ctccgacgtt aggtcaaaact tttccaagct    6840
ggtagacaca atcaaccaga tgcaggaaga catgtccaca aagcacggac ctgactttaa    6900
ccggttggtg tccgcttttg aggagttggc cactggagtg aaagccatca gtgaccggtct    6960
tgacgaggcc aagcccggt acaagcttat caagctcctg agccgccgt cgtgcatggc      7020
cgctgtggca gcacggtcaa aggacccagt ccttgtggcc atcatgctgg ctgacaccgg    7080
tctcgagatt ctggacagca ccttcgtcgt gaagaagatc tccgactcgc tctccagtct    7140
cttccacgtg ccggccccg tcttcagttt cggagcccg attctgttag ccgggttggt      7200
caaggtcgcc tcgagtttct tccggtccaa gcccgaagac cttgagagag cagagaaaca    7260
gctcaaagca cgtgacatca acgacatttt cgccattctc aagaacggcg agtggctggt    7320
caaattgatc cttgccatcc gcgactggat caaggcatgg atagcctcag aagaaaagtt    7380
tgtcaccacg acagacttgg tacctagcat ccttgaaaaa cagcaggacc tcaacgaccc    7440
aagcaagtac aaggaagcca aggagtggct cgacaacgcg cgccaagcgt gtttgaagag    7500
cgggaacgtc cacattgcca acctgtgcaa agtggtcgcc ccggcaccca gcaggtcgag    7560
acccgagccc gtggtcgttt gcctccgtgg caagtccggt cagggcaaga gtttccttgc    7620
aaacgtgctc gcacaagcaa tctctaccca tttcactggc aggaccgatt cagtttggta    7680
ctgcccgcct gaccctgacc acttcgacgg ttacaaccaa cagactgtcg ttgtgatgga    7740
cgatttgggc cagaaccccg acggcaaaga cttcaagtac ttcgcccaaa tggtttcaac    7800
aacgggttc atcccgccca tggtcatcgt tgaggataaa ggcaaaccct tcaacagtaa      7860
ggtcatcata gcaaccacca acctgtactc gggcttcacc ccgaggacta tggtgtgccc    7920
tgatgccctg aaccggaggt ttcactttga catcgacgtg agcgcaagg acgggtacaa     7980
aattaacaac aaattggaca tcatcaaagc acttgaagat actcacacca acccagtggc    8040
aatgtttcag tacgactgtg cccttctcaa cggcatggct gttgaaatga agagaatgca    8100
acaagatatg ttcaagcctc aaccaccct tcagaacgtg taccaactgg ttcaagaggt    8160
gattgagcgg gtgtggagctcc acgagaaggt gtcgagccac ccgattttca aacagatctc    8220
aattccttcc caaaaatccg tgttgtactt cctcattgag aaaggacagc acgaggcagc    8280
aattgaattc tttgagggca tggtgcacga ctccatcaag gaggagctcc ggccgctcat    8340
ccaacaaacc tcatttgtga aacgcgcttt taagcgcctg aaggaaaaact ttgagattgt    8400
tgccctatgt ctgacccctcc tggccaacat agtgactcat atccgcgaaa ctcgcaagag    8460
acagaagatg gtggacgatg cagtgagtga gtacattgag agagcaaaca tcaccaccga    8520
cgacaagact cttgatgagg cggaaaagaa ccctctggaa accagcggtg ccagcaccgt    8580
cggcttcaga gagagacctc tcccaggcca aaaggcgcgt aatgacgaga actccgagcc    8640
cgcccagcct gctgaagagc aaccacaagc tgaaggaccc tacgctggcc cgatggagag    8700
accagttaaa gttaaagtga aagcaaaagc cccggtcagg aaggaagac cttacgaggg     8760
accggtgaag aagcctgttg cttttgaaagt gaaagctaag aacttgatcg tcactgagag    8820
tggtgccccca ccgaccgact tgcaaaagtt ggtcatgggc aacaccaagc ccgttgagct    8880
catccttgac gggaagacgg tagccatttg ctgtgctact ggagttttcg gcactgctta    8940
cctcgtgcct cgtcatcttt tcgcagaaaa gtacgacaag atcatgttgg acggcagagc    9000
catgacagat agtgactaca gagtgtttga gtttgagatt aaagtaaaag gacaggacat    9060
```

```
gctctcagac gctgcgctca tggtgctcca ccgtgggaat cgcgtgagag acatcacgaa    9120
acactttcgt gacacagcaa gaatgaagaa aggcacccccc gtcgttggtg tgatcaacaa    9180
cgccgatgtc gggagactga tttctctgg tgaagcccctt acctacaagg acattgtagt    9240
gtgcatggat ggagacacca tgcctgggct ctttgcctac aaagccgcaa ccaaggctgg    9300
ttattgcgga ggagccgtcc tcgctaagga cggggcgac acgttcatcg ttggcaccca    9360
ctccgctgga ggcaatggcg ttggatactg ctcttgcgtt tccaggtcca tgcttctcaa    9420
gatgaaggca cacgttgacc ccgaaccaca ccacgagggg ttgattgttg acaccagaga    9480
tgtggaagag cgcgttcacg tgatgcgcaa aaccaagctt gcaccaccg ttgcgtacgg     9540
tgtgttccgt cctgagttcg ggcctgccgc ctttgtccaa aaggacccgc gcctgaacga    9600
cggtgttgtc ctcgacgaag tcatcttctc caaacacaag ggagacacaa agatgtctga    9660
ggaagacaaa gcgctgttcc gccgctgtgc tgctgactac gcgtcacgcc tgcacagcgt    9720
gttgggtacg gcaaatgccc cactgagcat ctacgaggca attaaggcg ttgatggact     9780
cgacgcaatg gaaccagaca ccgcaccgg cctccctgg gcactccagg ggaagcgccg      9840
tggcgcgctc atcgacttcg agaacggcac tgttgacacc gaagttgagg ctgccttgaa    9900
gctcatggag aaaagagaat acaagtttgc ttgccaaacc ttcctgaagg acgagattcg    9960
cccgatggag aaagtacgtg ccggtaagac tcgcattgtc gacgtcctac ctgttgaaca   10020
catcctctac accaggatga tgattggcag attttgtgca caaatgcact caaacaacg    10080
accccaaatt ggctcggcgg tcggttgtaa ccctgatgtt gattggcaaa gatttggcac   10140
acacttcgcc caatacgaaa acgtgtggga tgtggactat tcggccttcg atgctaacca   10200
ctgcagtgac gccatgaaca tcatgtttga ggaagtgttt cgcacagaat cgggttcca    10260
cccaaacgct gagtggatcc tgaagactct cgtgaacacg aacacgcct atgagaacaa    10320
acgcatcact gttgaaggcg ggatgccatc tggttgttcc gcaacaagca tcatcaacac   10380
aatttttgaac aacatctacg tgctctacgc tttgcgtaga cactatgagg gagttgagtc   10440
ggacacttac accatgatct cttacggaga cgatatcgtg gtggcaagtg attacgattt   10500
ggactttgag gctctcaagc cccacttcaa atcccttggt caaaccatca ctccagctga   10560
caaagcggac aaaggttttg ttcttggtca tccattacg tgtcactt tcctcaaaag      10620
acacttccac atggattatg gaactgggtt ttacaaacct gtgatggcct caaagacct    10680
tgaggctatc ctctcctttg cacgccgtgg gaccatacag gagaagttga tctccgtggc   10740
aggactcgct gttcactctg gaccagacga gtaccggcgt ctcttcgagc cctttcaagg   10800
cctcttcgag attccaagct acagatcact ttacctgcgt tgggtgaacg ccgtgtgcgg   10860
cgacgca                                                             10867

SEQ ID NO: 16            moltype = AA   length = 2109
FEATURE                  Location/Qualifiers
REGION                   1..2109
                         note = Fusion protein: Foot and Mouth Disease Virus (FMDV)
                         and Bovine Rhinovirus Type 2 (BRV2)
source                   1..2109
                         mol_type = protein
                         organism = synthetic construct
SEQUENCE: 16
GAGQSSPATG SQNQSGNTGS IINNYYMQQY QNSMDTQLGD NAISGGSNEG STDTTSTHTT     60
NTQNNDWFSK LASSAFTGLF GALLADKKTE ETTLLEDRIL TTRNGHTTST TQSSVGVTHG    120
YSTEEDHVAG PNTSGLETRV VQAERFYKKY LFDWTTDKAF GHLEKLELPS DHHGVFGHLV    180
DSYAYMRNGW DVEVSAVGNQ FNGGCLLVAM VPEWKEFDTR EKYQLTLFPH QFISPRTNMT    240
AHITVPYLGV NRYDQYKKHK PWTLVVMVVS PLTVNNTSAA QIKVYANIAP TYVHVAGELP    300
SKEGIFPVAC ADGYGGLVTT DPKTADPAYG KVYNPPRTNY PGRFTNLLDV AEACPTFLCF    360
DDGKPYVTTR TDDTRLLAKF DLSLAAKHMS NTYLSGIAQY YTQYSGTINL HFMFTGSTDS    420
KARYMVAYIP PGVETPPDTP ERAAHCIHAE WDTGLNSKFT FSIPYVSAAD YAYTASDTAE    480
TINVQGWVCI YQITHGKAEN DTLVVSVSAG KDFELRLPID PRQQTTATGE SADPVTTVE     540
NYGGETQIQR RHHTDIGFIM DRFVKIQSLS PTHVIDLMQT HQHGLVGALL RAATYYFSDL    600
EIVVRHEGNL TWVPNGAPES ALLNTSNPTA YNKAPFTRLA LPYTAPHRVL ATVYNGTSKY    660
AVGGSGRRGD MGSLAARVVK QLPASFNYGA IKADAIHELL VRMKRAELYC PRPLLAIEVS    720
SQDRHKQKII APAKQLLNFD LLKLAGDVES NPGPFFFSDV RSNFSKLVDT INQMEDMST     780
KHGPDFNRLV SAFEELATGV KAIRTGLDEA KPWYKLIKLL SRLSCMAAVA ARSKDPVLVA    840
IMLADTGLEI LDSTFVVKKI SDSLSSLFHV PAPVFSFGAP ILLAGLVKVA SSFFRSTPED    900
LERAEKQLKA RDINDIFAIL KNGEWLVKLI LAIRDWIKAW IASEEKFVTT TDLVPSILEK    960
QQDLNDPSKY KEAKEWLDNA RQACLKSGNV HIANLCKVVA PAPSRSRPEP VVVCLRGKSG   1020
QGKSFLANVL AQAISTHFTG RTDSVWYCPP DPDHFDGYNQ QTVVVMDDLG QNPDGKDFKY   1080
FAQMVSTTGF IPPMASLEDK GKPFNSKVII ATTNLYSGFT PRTMVCPDAL NRRFHFDIDV   1140
SAKDGYKINN KLDIIKALED THTNPVAMFQ YDCALLNGMA VEMKRMQQDM FKPQPPLQNV   1200
YQLVQEVIER VELHEKVSSH PIFKQISIPS QKSVLYFLIE KGQHEAAIEF FEGMVHDSIK   1260
EELRPLIQQT SFVKRAFKRL KENFEIVALC LTLLANIVIM IRETRKRQKM VDDAVSEYIE   1320
RANITTDDKT LDEAEKNPLE TSGASTVGFR ERPLPGQKAR NDENSEPAQP AEEQPQAEGP   1380
YAGPMERPVK VKVKAKAPVV KEGPYEGPVK KPVALKVKAK NLIVTESGAP PTDLQKLVMG   1440
NTKPVELILD GKTVAICCAT GVFGTAYLVP RHLFAEKYDK IMLDGRAMTD SDYRVFEFEI   1500
KVKGQDMLSD AALMVLHRGN RVRDITKHFR DTARMKKGTP VVGVINNADV GRLIFSGEAL   1560
TYKDIVVCMD GDTMPGLFAY KAATKAGYCG GAVLAKDGAD TFIVGTHSAG GNGVGYCSCV   1620
SRSMLLKMKA HVDPEPHHEG LIVDTRDVEE RVHVMRKTKL APTVAYGVFR PEFGPAALSN   1680
KDPRLNDGVV LDEVIFSKHK GDTKMSEEDK ALFRRCAADY ASRLHSVLGT ANAPLSIYEA   1740
IKGVDGLDAM EPDTAPGLPW ALQGKRRGAL IDFENGTVGP EVEAALKLME KREYKFACQT   1800
FLKDEIRPME KVRAGKTRIV DVLPVEHILY TRMMIGRFCA QMHSNNGPQI GSAVGCNPDV   1860
DWQRFGTHFA QYRNVWDVDY SAFDANHCSD AMNIMFEEVF RTEFGFHPNA EWILKTLVNT   1920
EHAYENKRIT VEGGMPSGCS ATSIINTILN NIYVLYALRR HYEGVELDTY TMISYGDDIV   1980
VASDYDLDFE ALKPHFKSLG QTITPADKSD KGFVLGHSIT DVTFLKRHFH MDYGTGFYKP   2040
VMASKTLEAI LSFARRGTIQ EKLISVAGLA VHSGPDEYRR LFEPFQGLFE IPSYRSLYLR   2100
WVNAVCGDA                                                           2109

SEQ ID NO: 17            moltype = DNA   length = 6327
```

| FEATURE | Location/Qualifiers |
|---|---|
| misc_feature | 1..6327 |
| | note = Fusion nucleotide: Foot and Mouth Disease Virus (FMDV) and Bovine Rhinovirus Type 2 (BRV2) |
| source | 1..6327 |
| | mol_type = other DNA |
| | organism = synthetic construct |

SEQUENCE: 17

```
ggggccggcc aatccagtcc ggcgaccggc tcgcagaacc aatctggcaa cactggcagc    60
ataattaaca actactacat gcagcaatac cagaactcca tggacacaca gttgggagac   120
aatgccatca gtggaggctc caacgagggc tccacggaca caacttcaac acacacaacc   180
aacactcaaa acaatgactg gttctcgaag ctcgccagtt cagcttttac cggtctgttc   240
ggtgcactgc tcgccgacaa gaagacgag gaaacgacac ttcttgagga ccgcatcctc   300
accacccgca acgggcacac cacctcgacg acccaatcga gtgtgggtgt cacacacggg   360
tactccacag aggaggacca cgttgctggg cccaacacat cgggcctgga gacgcgagtg   420
gtgcaggcag agagattcta caaaaagtac ttgtttgact ggacaacgga caaggcattt   480
ggacacctgg aaaagctgga gctcccgtcc gaccaccacg gtgtctttgg acacttggtg   540
gactcgtacg cctatatgag aaatggctgg gatgttgagg tgtccgctgt tggcaaccag   600
ttcaacggcg ggtgcctcct ggtgccatg gtacctgaat ggaaggaatt tgacacacgg   660
gagaaatacc aactcaccct tttcccgcac cagtttatta gccccagaac taacatgact   720
gcccacatca cggtcccta ccttggtgtg aacaggtatg atcagtacaa gaagcataag   780
ccctggacat tggttgtcat ggtcgtgtcg ccacttcgtg tcaacaacac tagtgcggca   840
caaatcaagg tctacgccaa catagctccg acctatgttc acgtggccgg tgaactcca   900
tcgaaagagg ggattttccc ggttgcatgt gcggacggtt acggaggatt ggtgacgaca   960
gaccccgaaga cagctgaccc tgcttatggc aaggtgtaca acccgcctag gactaactac  1020
cctgggcgct tcaccaacct gttggacgtg gccgaagcgt gtcccacttt cctctgcttt  1080
gacgacggga aaccgtacgt caccacgcgg acgatgaca cccgacttt ggccaagttt  1140
gactttcccc ttgccgcaaa acatatgtcc aacacatacc tgtcaggat tgctcagtac  1200
tacacacagt actctggcac catcaatttg catttcatgt tcacaggttc cactgattca  1260
aaggcccgat acatggtggc ctacatccca cctggggtgg agacaccacc ggacacacct  1320
gaaagggctg cccactgcat tcacgctgaa tgggacactg gactaaactc caaattcact  1380
ttctcaatcc cgtacgtatc cgccgcggat tacgcgtaca cagcgtctga cacggcagaa  1440
acaatcaacg tacagggatg ggtctgcatc taccaaatta cacacgggaa ggctgaaaat  1500
gacaccttgg tcgtgtcggt tagcgccggc aaagacttttg agttgcgcct cccgattgac  1560
ccccgccagc agaccaccgc taccggggaa tcagcagacc cggtcaccac caccgtggag  1620
aactacggcg gtgagacaca aatccagaga cgtcaccaca cggacattgg tttcatcatg  1680
gacagatttg tgaagatcca aagcttgagc ccaacacatg tcattgacct catgcagact  1740
caccaacacg gtctggtggg tgcttctctg cgtgcagcca cgtactactt ttctgacctg  1800
gaaattgttg tacggcacga aggcaatctg acctgggtgc ccaacggcgc ccctgaatca  1860
gccctgttga caccagcaa cccccactgc ctacaacaagg caccattcac gagactcgct  1920
ctcccctaca ctgcgccgca ccgtgtgctg gcaacagtgt acaacgggac gagtaagtat  1980
gctgtgggtg gttcaggcag aagaggcgac atggggtctc tcgcggcgcg agtcgtgaaa  2040
cagcttcctg cttcatttaa ctacggtgca atcaaggccg acgccatcca cgaacttctc  2100
gtgcgcatga acgggccgga gctctactgc cccagaccgc tgttggcaat agaggtgtct  2160
tcgcaagaca ggcacaagca aaagatcatt gcaccagcaa agcagcttct gaattttgac  2220
ctgcttaagc tagccggaga cgttgagtcc aaccctgggc ccttcttctt ctccgacgtt  2280
aggtcaaact tttccaagct ggtagacaca atcaaccaga tggaagaa catgtccaca  2340
aagcacggac ctgactttaa ccggttggtg tccgcttttg aggagttggc cactggagtg  2400
aaaagccatca ggaccggtct tgacgaggcc aagcccggt acaagcttat caagctcctg  2460
agccgcctgt cgtgcatggc cgctgtggca gcacggtcaa aggacccagt ccttgtggcc  2520
atcatgctgc ctgacaccgg tctcgagatt ctggacagca ccttcgtcgt gaagaagtct  2580
tccgactcgc tctccagtct cttccacgtg ccggcccccg tcttcagttt cggagccccg  2640
attctgttag ccgggttggt caaggtcgcc tcgagtttct tccggtccac gcccgaagac  2700
cttgagagag cagagaaaca gctcaaagca cgtgacatca cgacatttt cgccattctc  2760
aagaacggcg agtggctggt caaattgatc cttgccatcc gcgactggat caaggcatgg  2820
atagcctcag aagaaaagtt tgtcaccacg acagactgg tacctagcat ccttgaaaaa  2880
cagcaggacc tcaacgaccc aagcaagtac aaggaagcca aggagtggct cgacaacgcg  2940
cgccaagcgt gtttgaagag cgggaacgtc acattgcca acctgtgcaa agtggtcgcc  3000
ccggcaccca gcaggtcgag acccgagccc gtggtcgttt gcctccgtgg caagtccggt  3060
cagggcaaga gtttccttgc aaacgtgctc gcacaagcaa tctctaccca tttcactggg  3120
aggaccgatt cagtttggta ctgcccgcct gaccctgacc acttcgacgg ttacaaccaa  3180
cagactgtcg ttgtgatgga cgatttgggc cagaaccccg acgcaaaga cttcaagtac  3240
ttcgcccaaa tggttttcaac aacggggttc atccgcccca tggcatcgct gaggataaa  3300
ggcaaaccct tcaacagtaa ggtcatcata gcaaccacca accggccctc gggcttcacc  3360
ccgaggacta tggtgtgccc tgatgccctg aaccggaggt tcacttttga catcgacgtg  3420
agcgccaagg acgggtacaa aattaacaac aaattggaca tcatcaaagc acttgaagat  3480
actcacacca accccagtggc aatgtttcag tacgactgtg cccttctcaa cggcatggct  3540
gttgaaatga gagaatgca acaagatatg ttcaagcctc aaccaccct tcagaacgtg  3600
taccaactgg ttcaagaggt gattgagcgg gtggagctcc acgagaaggt gtcgagccac  3660
ccgatttttca aacagatctc aattccttcc caaaaatccg tgttgtactt cctcattgag  3720
aaaggacagc acgaggcagc aattgaattc tttgagggca tggtgcacga ctccatcaag  3780
gaggagctcc ggccgctcat ccaacaaacc tcatttgtga acgcgcttt taagcgcctg  3840
aaggaaaact ttgagattgt tgcccctatgt ctgaccctcc tggccaacat agtgatcatg  3900
atccgcgaaa tcgccaagag acagaagatg gtggacagtg cagtgagtga gtacattgag  3960
agagcaaaca tcaccaccga cgacaagact cttgatgagg cggaaagaa ccctctggaa  4020
accagccggtg ccagcaccgt cggcttcaga gagaggacctc tccaggcca aaggcgcgt  4080
aatgacgaga actccgagcc cgcccagcct gctgaagagc aaccacagc tgaaggaccc  4140
tacgctggcc cgatggagag acagaaacca ctgaaagtga agcaaaagc cccggtcgtt  4200
aaggaaggac cttacgaggg accggtgaag aagcctgttg ctttgaaagt gaaagctaag  4260
```

```
aacttgatcg tcactgagag tggtgcccca ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag gacaggacat gctctcagac gctgcgctca tggtgctcca ccgtgggaat    4560
cgcgtgagag acatcacgaa acactttcgt gacacagcaa gaatgaagaa aggcaccccc    4620
gtcgttggtg tgatcaacaa cgccgatgtc gggagactga ttttctctgg tgaagccctt    4680
acctacaagg acattgtagt gtgcatggat ggagacacca tgcctgggct ctttgcctac    4740
aaagccgcaa ccaaggctgg ttattgcgga ggagccgtcc tcgctaagga cggggctgac    4800
acgttcatcg ttggcaccca ctccgctgga ggcaatgacg ttggatactg ctcttgcgtt    4860
tccaggtcca tgcttctcaa gatgaaggca cacgttgacc ccgaaccaca ccacgagggg    4920
ttgattgttg acaccagaga tgtggaagag cgcgttcacg tgatgcgcaa aaccaagctt    4980
gcacccaccg ttgcgtacgg tgtgttccgt cctgagttcg gcctgccgc cttgtccaac    5040
aaggacccgc gcctgaacga cggtgttgtc ctcgacgaag tcatcttctc caaacacaag    5100
ggagacacaa agatgtctga ggaagacaaa gcgctgttcc gccgctgtgc tgctgactac    5160
gcgtcacgcc tgcacagcgt gttgggtacg gcaaatgccc cactgagcat ctacgaggca    5220
attaaaggcg ttgatggact cgacgcaatg gaaccagaca ccgcacccgg cctccctgg    5280
gcactccagg ggaagcgccg tggcgcgctc atcgacttcg agaacggcac tgttggaccc    5340
gaagttgagg ctgccttgaa gctcatggag aaaagagaat acaagtttgc ttgccaaacc    5400
ttcctgaagg acgagattcg cccgatggag aaagtacgtg ccggtaagac tcgcattgtc    5460
gacgtcctac ctgttgaaca catcctctac accaggatga tgattggcag attttgtgca    5520
caaatgcact caaacaacgg accccaaatt ggctcggcgg tcggttgtaa ccctgatgtt    5580
gattggcaaa gatttggcac acacttcgcc caatacagaa acgtgtggga tgtggactat    5640
tcggccttcg atgctaacca ctgcagtgac gccatgaaca tcatgtttga ggaagtgttt    5700
cgcacagaat tcgggttcca cccaaacgct gagtggatcc tgaagactct cgtgaacacg    5760
gaacacgcct atgagaacaa acgcatcact gttgaaggcg ggatgccatc tggttgttcc    5820
gcaacaagca tcatcaacac aattttgaac aacatctacg tgctctacgc tttgcgtaga    5880
cactatgagg gagttgagct ggacacttac accatgatct cttacggaga cgatatcgtg    5940
gtggcaagtg attacgattt ggactttgag gctctcaagc cccacttcaa atcccttggt    6000
caaaccatca ctccagctga caaaagcgac aaaggttttg ttcttggtca ctccattact    6060
gatgtcactt tcctcaaaag acacttccac atggattatg gaactgggtt ttacaaacct    6120
gtgatggcct caaagaccct tgaggctatc ctctcctttg cacgccgtgg gaccatacag    6180
gagaagttga tctccgtggc aggactcgct gttcactctg gaccagacga gtaccggcgt    6240
ctcttcgagc cctttcaagg cctcttcgag attccaagct acagatcact ttacctgcgt    6300
tgggtgaacg ccgtgtgcgg cgacgca                                         6327
```

```
SEQ ID NO: 18          moltype = AA   length = 2109
FEATURE                Location/Qualifiers
REGION                 1..2109
                       note = Fusion protein: Foot and Mouth Disease Virus (FMDV)
                       and Bovine Rhinovirus Type 2 (BRV2)
source                 1..2109
                       mol_type = protein
                       organism = synthetic construct SEQUENCE: 18
GAGQSSPATG  SQNQSGNTGS  IINNYYMQQY  QNSMDTQLGD  NAISGGSNEG  STDTTSTHTT    60
NTQNNDWFSK  LASSAFTGLF  GALLADKKTE  ETTLLEDRIL  TTRNGHTTST  TQSSVGVTHG   120
YSTEEDHVAG  PNTSGLETRV  VQAERFYKKY  LFDWTTDKAF  GHLEKLELPS  DHHGVFGHLV   180
DSYAYMRNGW  DVEVSAVGNQ  FNGGCLLVAM  VPEWKEFDTR  EKYQLTLFPH  QFISPRTNMT   240
AHITVPYLGV  NRYDQYKKHK  PWTLVVMVVS  PLTVNNTSAA  QIKVYANIAP  TYVHVAGELP   300
SKEGIFPVAC  ADGYGGLVTT  DPKTADPAYG  KVYNPPRTNY  PGRFTNLLDV  AEACPTFLCF   360
DDGKPYVTTR  TDDTRLLAKF  DLSLAAKHMS  NTYLSGIAQY  YTQYSGTINL  HFMFTGSTDS   420
KARYMVAYIP  PGVETPPDTP  ERAAHCIHAE  WDTGLNSKFT  FSIPYVSAAD  YAYTASDTAE   480
TINVQGWVCI  YQITHGKAEN  DTLVVSVSAG  KDFELRLPID  PRQQTTATGE  SADPVTTTVE   540
NYGGETQIQR  RHHTDIGFIM  DRFVKIQSLS  PTHVIDLMQT  HQHGLVGALL  RAATYYFSDL   600
EIVVRHEGNL  TWVPNGAPES  ALLNTSNPTA  YNKAPFTRLA  LPYTAPHRVL  ATVYNGTSKY   660
AVGGSGRRGD  MGSLAARVVK  QLPASFNYGA  IKADAIHELL  VRMKRAELYC  PRPLLAIEVS   720
SQDRHKQKII  APAKQLLNFD  LLKLAGDVES  NPGPFFFSDV  RSNFSKLVDT  INQMEDMST   780
KHGPDFNRLV  SAFEELATGV  KAIRTGLDEA  KPWYKLIKLL  SRLSCMAAVA  ARSKDPVLVA   840
IMLADTGLEI  LDSTFVVKKI  SDSLSSLFHV  PAPVFSFGAP  ILLAGLVKVA  SSFFRSTPED   900
LERAEKQLKA  RDINDIFAIL  KNGEWLVKLI  LAIRDWIKAW  IASEEKFVTT  TDLVPSILEK   960
QQDLNDPSKY  KEAKEWLDNA  RQACLKSGNV  HIANLCKVVA  PAPSRSRPEP  VVVCLRGKSG  1020
QGKSFLANVL  AQAISTHFTG  RTDSVWYCPP  DPDHFDGYNQ  QTVVVMDDLG  QNPDGKDFKY  1080
FAQMVSTTGF  IPPMASLEDK  GKPFNSKVII  ATTNLYSGFT  PRTMVCPDAL  NRRFHFDIDV  1140
SAKDGYKINN  KLDIIKALED  THTNPVAMFQ  YDCALLNGMA  VEMKRMQQDM  FKPQPPLQNV  1200
YQLVQEVIER  VELHEKVSSH  PIFKQISIPS  QKSVLYFLIE  KGQHEAAIEF  FEGMVHDSIK  1260
EELRPLIQQT  SFVKRAFKRL  KENFEIVALC  LTLLANIVIM  IRETRKRQKM  VDDAVSEYIE  1320
RANITTDDKT  LDEAEKNPLE  TSGASTVGFR  ERPLPGQKAR  NDENSEPAQP  AEEQPQAEGP  1380
YAGPMERQKP  LKVKAKAPVV  KEGPYEGPVK  KPVALKVKAK  NLIVTESGAP  PTDLQKLVMG  1440
NTKPVELILD  GKTVAICCAT  GVFGTAYLVP  RHLFAEKYDK  IMLDGRAMTD  SDYRVFEFEI  1500
KVKGQDMLSD  AALMVLHRGN  RVRDITKHFR  DTARMKKGTP  VVGVINNADV  GRLIFSGEAL  1560
TYKDIVVCMD  GDTMPGLFAY  KAATKAGYCG  GAVLAKDGAD  TFIVGTHSAG  GNGVGYCSCV  1620
SRSMLLKMKA  HVDPEPHHEG  LIVDTRDVEE  RVHVMRKTKL  APTVAYGVFR  PEFGPAALSN  1680
KDPRLNDGVV  LDEVIFSKHK  GDTKMSEEDK  ALFRRCAADY  ASRLHSVLGT  ANAPLSIYEA  1740
IKGVDGLDAM  EPDTAPGLPW  ALQGKRRGAL  IDFENGTVGP  EVEAALKLME  EREYKFACQT  1800
FLKDEIRPME  KVRAGKTRIV  DVLPVEHILY  TRMMIGRFCA  QMHSNNGPQI  GSAVGCNPDV  1860
DWQRFGTHFA  QYRNVWDVDY  SAFDANHCSD  AMNIMFEEVF  RTEFGFHPNA  EWILKTLVNT  1920
EHAYENKRIT  VEGGMPSGCS  ATSIINTILN  NIYVLYALRR  HYEGVELDTY  TMISYGDDIV  1980
VASDYDLDFE  ALKPHFKSLG  QTITPADKSD  KGFVLGHSIT  DVTFLKRHFH  MDYGTGFYKP  2040
```

```
VMASKTLEAI LSFARRGTIQ EKLISVAGLA VHSGPDEYRR LFEPFQGLFE IPSYRSLYLR    2100
WVNAVCGDA                                                            2109

SEQ ID NO: 19            moltype = AA  length = 40
FEATURE                  Location/Qualifiers
REGION                   1..40
                         note = Foot-and-mouth disease virus
source                   1..40
                         mol_type = protein
                         organism = synthetic construct
SEQUENCE: 19
GLIVDTRDVE ERVHVMRKTK LAPTVAHGVF NPEFGPAALS                           40

SEQ ID NO: 20            moltype = AA  length = 40
FEATURE                  Location/Qualifiers
REGION                   1..40
                         note = Foot-and-mouth disease virus
source                   1..40
                         mol_type = protein
                         organism = synthetic construct
SEQUENCE: 20
GLIVDTRDVE ERVHVMRKTK LAPTVAYGVF RPEFGPAALS                           40

SEQ ID NO: 21            moltype = AA  length = 24
FEATURE                  Location/Qualifiers
REGION                   1..24
                         note = Foot-and-mouth disease virus
source                   1..24
                         mol_type = protein
                         organism = synthetic construct
SEQUENCE: 21
GPYAGPMERQ KPLKVRAKAP VVKE                                            24

SEQ ID NO: 22            moltype = AA  length = 24
FEATURE                  Location/Qualifiers
REGION                   1..24
                         note = Foot-and-mouth disease virus
source                   1..24
                         mol_type = protein
                         organism = synthetic construct
SEQUENCE: 22
GPYAGPMEPV KVLKVRAKAP VVKE                                            24

SEQ ID NO: 23            moltype = DNA  length = 7589
FEATURE                  Location/Qualifiers
misc_feature             1..7589
                         note = Fusion nucleotide: Foot and Mouth Disease Virus
                         (FMDV) and Bovine Rhinovirus Type 2 (BRV2)
source                   1..7589
                         mol_type = other DNA
                         organism = synthetic construct
SEQUENCE: 23
ttgaaagggg gcgctagggt ctcaccccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg gcgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
ctttcacccc cccccccccc cccccccccc cccccccctaa gttctaccgt              420
cgttcccgac gtaaagggat gtaaccacaa gcttactacc gcctttcccg gcgttaaagg    480
gatgtaacca caagacttac cttcacccgg aagtaaaacg gcaacttcac acagttttgc    540
ccgttttcat gagaaatggg acgtctgcgc acgaaacgcg ccgtcgcttg aggaggactt    600
gtacaaaacac gatctaagca ggtttcccca actgacacaa accgtgcaat ttgaaactcc   660
gcctgggctt tccaggtcta gaggggtgac gctttgtact gtgtttgact ccacgttcga    720
tccactggcg agtgttagta acaacactgc tgcttcgtag cggagcatga cggccgtggg    780
acccccccccc ttggtaacaa ggaccccagg ggccaaaagc cacgtccgaa tggacccgtc   840
atgtgtgcaa acccagcaca gtagcttcgt tgtgaaactc actttaaagt gacattgata    900
ctggtactca agcactggtg acaggctaag gatgccctttc aggtaccccg aggtaacacg   960
tgacactcgg gatctgagaa gggggacccggg gcttctataa aagcgccccgg ttttaaaaagc 1020
ttctatgtct gaataggtga ccggaggccg gcacctttct tttaattaca ctggacttat    1080
gaacacaact gattgtttta tcgctttggt acacgctatc agagagatca gagcattttt   1140
cctaccacga gccacaggaa tggggccggg ccaatccagt ccggcaaccg ggtcacgaa    1200
ccaatctggc aacactggaa gcatcattaa caactactac atgcaacagt accagaattc    1260
catggacaca cagcttggtg acaacgctat tagcggaggt tccaacgaag gttccacgga   1320
taccacttcc acacacacaa acaacaccca aaacaacgac tggttctcgc gcctggcaag   1380
ttctgcattc agtggtctct ttggtgcact tttggctgac aagaagacag aagagacaac    1440
tctgcttgaa gaccgcattc tcaccaccag gaacggccac acaacatcga cgacacagtc    1500
gagcgttggc gtaacatacg gttacgctgt ggccgaggac gcggtgtctg acccaatac    1560
ctcgggtcta gagactcgtg ttcaacaggc agaacggttt tcaagaaac acctgtttga    1620
```

```
ctggacaccg aacttggcat ttggacactg ttactacctg gaacttccca ctgaacacaa    1680
aggcgtgtac ggcagtctca tgggctcgta cgcctacatg agaaatggat gggacataga    1740
ggtgactgct gttggaaacc aattcaacgg tggttgtctc cttgtcgcgc tcgtgccaga    1800
gctgaaggaa ctcgacacgc gacagaagta ccagctgacc ctctttcccc accagttcat    1860
caacccacgc accaacatga cggcccacat caacgtgcta tacgtgggta tcaacaggta    1920
cgaccagtac gccctccaca agccgtggac gcttgttgtg atggtggtag ccccactcac    1980
cgtcaaaact ggtggttctg aacagatcaa ggtttacatg aatgcagcgc aacctacgt     2040
gcatgtggcg ggagagctgc cctcgaaaga gggaatagtt cccgtcgcgt gtgcggacgg    2100
ttacggcaac atggtgacca cggacccgaa gacggccgat ccagtttacg ggaaagtgtt    2160
caaccccccc aggacaaacc tccctgggcg cttcacgaac ttccttgatg ttgcggaggc    2220
atgtccaact ttcctccgct ttggagaagt accatttgtg aagacggtga actctggtga    2280
ccgcttgctg gccaagttcg acgtgtccct cgctgcaggg cacatgtcca cacctactt    2340
ggctggcctg gcgcagtact acacacagta cagcggcacc atgaacgtcc acttcatgtt    2400
caccggcacc acggatgcta aagcccgata catggtggct tatgtccccc ctggcatgac    2460
accgccacg gaccctgagc acgccgcaca ctgcattcac tctgagtggg atactggtct    2520
taactctaag tttacctttt ccatacctta cctctctgct gctgactatg cctacactgc    2580
ttctgacgtg cggagacca cgagtgtgca gggatgggtg tgtatctatc agatcaccca    2640
cggcaaggct gagggagacg cactggtcgt ttctgtcagc gccggcaaag actttgagtt    2700
tcgcttgcct gttgacgcac gccagcaaac caccaccact ggcgaatcag cagatccagt    2760
cacaaccacg gttgagaact atggaggaga gactcagaca gccagacggc ttcacactga    2820
cgtcgccttc attcttgaca ggtttgtgaa actcactgct cccaagaaca tccaaacct    2880
cgatctcatg cagatcccct cacacacgct ggttggagca ctacttcgtt ctgcgacgta    2940
ctacttctca gacctggagg tcgcgcttgt ccacacaggc ccggtcacct gggtgcccaa    3000
cggcgcgccc aaggatgctc taaacaacca gaccaaccca actgcctatc agaagcaacc    3060
catcacccgc ctggcactcc cctacaccgc cccccatcgt gtgctggcaa cagtgtacaa    3120
cgggaagacg gcgtacgggg aaacgacctc aaggcgcggc gcatggcgg ccctcgcaca    3180
aaggttgagc gctcggctgc ccacctcctt caactacggc gccgtgaagg ccgacaccat    3240
cactgagctt ttgatccgca tgaagcgcgc ggagacatat tgccctaggc ctttactagc    3300
ccttgacacc actcaggacc gccgcaaaca ggagatcatt gcacctgaga agcagcttct    3360
gaattttgac ctgcttaagc tagccggaca cgttgagtcc aaccctggc ccttcttctt    3420
ctccgacgtt aggtcaaact tttccaagct ggtagacaca atcaaccaga tgcaggaaga    3480
catgtccaca aagcacggac ctgactttaa ccggttggtg tccgcttttg aggagttggc    3540
cactggagtg aaagccatca ggaccggtct tgacagggcc aagccctggt acaagcttat    3600
caagctcctg agccgctgt cgtgcaggc cgctgtggca gcacggtcaa aggacccagt    3660
ccttgtggcc atcatgctgg ctgacaccgg tctcgagatt ctgacacagca ccttcgtcgt    3720
gaagaagatc tccgactcgc tctccagtct cttccacgtg ccggcccccg tcttcagttt    3780
cggagccccg attctgttag ccgggttggt caaggtcgcc tcgagtttct tccggtccac    3840
gccccgaagac cttgagagag cagagaaaca gctcaaagca cgtgacatca acgacatttt    3900
cgccattctc aagaacgcg agtggcctgt caaattgatc cttgccatcc gcgactggt    3960
caaggcatgg atagcctcag aagaaaagtt tgtcaccacg acagacttgg tacctagcat    4020
ccttgaaaaa cagcaggacc tcaacgaccc aagcaagtac aaggaagcca aggagtggct    4080
cgacaacgcg cgccaagcgt gtttgaagag cgggaacgtc cacattgcca acctgtgcaa    4140
agtggtcgcc ccggcaccca gcaggtcgag acccgagtgc gtggtcgttt gcctccgtgg    4200
caagtccggt cagggcaaga gttttccttgc aaacgtgctc gcacaagcaa tctctacccca   4260
tttcactggc aggaccgatt cagtttggta ctgcccgcct gaccctgacc acttcgacgg    4320
ttacaaccaa cagactgtcg ttgtgatgga cgatttgggc cagaaccccg acggcaaaga    4380
cttcaagtac ttcgcccaaa tggttcaac aacggggttc tcgccgccca tggcatcgct    4440
tgaggataaa ggcaaaccct tcaacagtaa ggtcatcata gcaaccacca acctgtactc    4500
gggcttcacc ccgaggacta tggtgtgccc tgatgccctg aaccggaggt ttcactttga    4560
catcgacgtg agcgccaagg acgggtacaa aattaacaac aaattggaca tcatcaaagc    4620
acttgaagat actcacacca acccagtggc aatgtttcag tacgactgtg ccttctcaa    4680
cggcatggct gttgaaatga agagaatgca acaagatatg ttcaagcctc aaccacccct    4740
tcagaacgtg taccaactgg ttcaagaggt gattgagcgg gtggagctcc acgagaaggt    4800
gtcgagccac ccgattttca acagatctc aattccttcc caaaaatccg tgttgtactt    4860
cctcattgag aaaggacagc acgaggcagc aattgaattc tttgagggga tggtgcacga    4920
ctccatcaag gaggagctcc ggccgctcat ccaacaaacc tcatttgtga acgcgcttt    4980
taagcgcctg aaggaaaact ttgagattgt tgccctatgt ctgaccctcc tggcaacat     5040
agtgatcatg atccgcgaaa ctcgcaagag acagaagatg gtggacgatg cagtgagtga    5100
gtacattgag agagcaaaca tcaccaccga cgacaagact cttgatgagg cggaaaagaa    5160
ccctctggaa accagcggtg ccagcaccgt cggcttcaga gagagacctc tcccaggcca    5220
aaaggcgcgt aatgacgaga actccgagcc cgcccagcct gctgaagagc aaccacaagc    5280
tgaaggaccc tacgctggcc cgatggagag accagttaaa gttaaagtga agcaaaagc    5340
cccggtcgtt aaggaaggac cttacgaggg accggtgaag aagcctgttg ctttgaaagt    5400
gaaagctaag aacttgatcg tcactgagag tggtgcccca ccgaccgact tgcaaaagtt    5460
ggtcatgggc aacaccaagc ccgttgagct catccttgac gggaagacgg tagccattg     5520
ctgtgctact ggagtttttcg gcactgctta cctcgtgcct cgtcatcttt tcgcagaaaa    5580
gtacgacaag atcatgttgg acggcagagc catgacagat agtgactaca gagtgtttga    5640
gtttgagatt aaagtaaaag gacaggcat gctctcagac gctgcgctca tggtgctcca    5700
ccgtgggaat cgcgtgagag acatcacgaa acactttgac agcacagca gaatgaagaa    5760
aggcaccccc gtcgttggtg tgatcaacaa cgccgatgtc gggagactga ttttctctgg    5820
tgaagccctt acctacaagg acattgtagt gtgcatggat ggagacacca tgcctgggct    5880
cttttgcctac aaagccgcaa ccaaggctgg ttattgcgga ggagccgtcc tcgctaagga    5940
cggggctgac acgttcatcg ttggcacca ctccgctgga ggcaatggcg ttggatactg    6000
ctcttgcgtt tccaggtcca tgcttctcaa gatgaaggca cagggtgacc ccgaaccaca    6060
ccacgagggg ttgattgttg acaccagaga tgtggaagag cgcgttcacg tgatgcgcaa    6120
aaccaagctt gcaccaccg ttgcgtacgg tgtgttccgt cctgagttcg ggcctgccgc    6180
cttgtccaac aaggacccgc gcctgaacga cggtgttgtc ctcgacgaag tcatcttctc    6240
caaacacaag ggagacacaa agatgtctga ggaagacaaa gcgctgttcc gccgctgtgc    6300
tgctgactac gcgtcacgcc tgcacagcgt gttgggtacg gcaaatgccc cactgagcat    6360
```

```
ctacgaggca attaaaggcg ttgatggact cgacgcaatg gaaccagaca ccgcacccgg  6420
cctcccctgg gcactccagg ggaagcgccg tggcgcgctc atcgacttcg agaacggcac  6480
tgttggaccc gaagttgagg ctgccttgaa gctcatggag aaaagagaat acaagtttgc  6540
ttgccaaacc ttcctgaagg acgagattcg cccgatggag aaagtacgtg ccggtaagac  6600
tcgcattgtc gacgtcctac ctgttgaaca catcctctac accaggatga tgattggcag  6660
attttgtgca caaatgcact caaacaacg accccaaatt ggctcggcgg tcggttgtaa  6720
ccctgatgtt gattggcaaa gatttggcac acacttcgcc caatacagaa acgtgtggga  6780
tgtggactat tcggccttcg atgctaacca ctgcagtgac gccatgaaca tcatgtttga  6840
ggaagtgttt cgcacagaat tcgggttcca cccaaacgtc gagtggatcc tgaagactct  6900
cgtgaacacg gaacacgcct atgaagaacaa acgcatcact gttgaaggcg ggatgccatc  6960
tggttgttcc gcaacaagca tcatcaacac aatttttgaac aacatctacg tgctctacgc  7020
tttgcgtaga cactatgagg gagttgagct ggacacttac accatgatct cttacggaga  7080
cgatatcgtg gtggcaagtg attacgattt ggactttgag gctctcaagc cccacttcaa  7140
atcccttggt caaaccatca ctccagctga caaaagcgac aaaggttttg ttcttggtca  7200
ctccattact gatgtcactt tcctcaaaag acacttccac atggattatg gaactgggtt  7260
ttacaaacct gtgatggcct caaagaccct tgaggctatc ctctccttg cacgccgtgg  7320
gaccatacag gagaagttga tctccgtggc aggactcgct gttcactctg accagacga  7380
gtaccggcgt ctcttcgagc cctttcaagg cctcttcgga attccaagct acagatcact  7440
ttacctgcgt tgggtgaacg ccgtgtgcgc cgacgcataa tccctcagag actacattgg  7500
catactgttt ctgaggcgcg cgacgccgta ggagtgaaaa gcctgaaagg gcttttcccg  7560
cttcctattc caaaaaaaaa aaaaaaaa                                    7589

SEQ ID NO: 24          moltype = DNA  length = 7600
FEATURE                Location/Qualifiers
misc_feature           1..7600
                       note = Fusion nucleotide: Foot and Mouth Disease Virus
                       (FMDV) and Bovine Rhinovirus Type 2 (BRV2)
source                 1..7600
                       mol_type = other DNA
                       organism = synthetic construct
SEQUENCE: 24
ttgaaagggg gcgctagggt ctcacccta gcatgccaac gacagtcccc gcgttgcact  60
ccacactcac gttgtgcgtg cgcggagctc gatggactat cgttcaccca cctacagctg  120
gactcacggc accgtgtggc cacttggctg gattgtgcgc acgaacaccg cttgcgcttc  180
tcgcgtgacc ggttagtact ctcaccacct tccgcccact tggttgttag cgctgtcttg  240
ggcactcctg ttgggggccg ttcgacgctc cgcgagtttc cccgcacggc aactacggtg  300
atggggccgt accgcgcggg ctgatcgcct ggtgtgcttc ggctgtcacc cgaagcctac  360
cttcccacccc ccgcccccc ccccccccc cccccccta agttctaccgt  420
cgttcccgac gtaaagggat gtaaccacaa gcttactacc gccttttccg gcgttaaagg  480
gatgtaacca caagacttac cttcacccgg aagtaaaacg gcaacttcac acagtttgc  540
ccgttttcat gagaaatggg acgtctgcgc acgaaacgcg ccgtcgcttg aggaggactt  600
gtacaaaac gatctaagca ggtttcccca actgacacaa accgtgcaat ttgaaactcc  660
gcctgggctt tccaggtcta gaggggtgac gctttgtact gctttgtact ccacgttcga  720
tccactggcg agtgttagta acaacactgc tgcttcgtag cggagcatga cggccgtggg  780
accccccccc ttggtaacaa ggaccacgg ggccaaaagc cacgtccgaa tggacccgtc  840
atgtgtgcaa acccagcaca gtagcttgt tgtgaaactc acttaaagt gacattgata  900
ctggtactca agcactggtg acagctaag gatgcccttc aggtaccccg aggtaacacg  960
tgacactcgg gatctgagaa ggggaccggg gcttctataa aagcgcccgg ttaaaaagc  1020
ttctatgtct gaataggtga ccggaggccg gcaccttttct tttaattaca ctggacttat  1080
gaacacaact gattgtttta tcgcttggt acacgctatc agagagatca gagcatttt  1140
cctaccacga gccacaggaa tgggggccgg ccaatccagt ccggcaaccg ggtcacaaa  1200
ccaatcaggc aacactggta gtatcatcaa caactactac atgcagcagt accagaactc  1260
catggataca caacttggcg acaacgccat tagcggtggt tccaacgagg ctccactga  1320
cactacctcc acacacacaa ccaacacaca gaacaatgac tggttttcaa agctggccag  1380
ttctgcttc agcggtctct tcggcgctct tctcgctgac aaaaagacag aggagactac  1440
cctcctggag gaccgcatcc ttaccacccg caacgacac accacctcga caacccagtc  1500
gagtgtgggt gtcacctacg gtactccac tggtgaagac cacgtctctg gacctaacac  1560
atctggcctg gagacgcgag tggtacaggc agagagattc ttcaagaaac acttgtttga  1620
ttggacaact gataaagctt tggacaccct ggaaaaactg gaatccca ccgaacaacaa  1680
gggtgtctac gggcacttgg tggactcttt cgcatacatg agaaatggct gggacgtgaa  1740
ggtgaccgcc gttggcaacc agttcaacgg tgggtgtctc ctggtggcca tggtacctga  1800
gtggaaaagag tttacccctc gtgagaaata ccagctcacc ctgtttccac caaatttat  1860
caaccccaga accaacatga cagcccacat acggtcccg taccttggtg tcaataggta  1920
tgaccagtac aaacagcaca aaccctggac actggtcggt atggtggttt cgccactgac  1980
caccagcagc attggggcct cacagattaa ggtctacgac aacattgccc caaccttcgt  2040
tcacgtggcc ggcgagctcc catcgaaaga agggatcgtg ccggttgctt gtacagacgg  2100
gtacggtggc ctggtgacaa cagacccgaa acagctgac cctgtttatg gtatggtgta  2160
caacccgccc agaaccaact accctgggcg ctttacaaca ttgttggacg tggccgaggc  2220
ttgcccgacc ttcctgtgtt ttgacgacgg gaaaccgtac gttgtgacaa ggacggacga  2280
ccaacgcctc ctggccaagt ttgacgtttc ccttgctgca aagcacatgt caaacaccta  2340
cctctcaggg atagcacagt actacacgca gtactctggc actatcaatc tgcatttcat  2400
gttcactggc tctactgaat caaaggcccg gtacatggtg gcgtacattc cacctggcat  2460
ggacaaccca ccggacacac ctgagaaggc tgcacattgc atccacgccg agtgggacac  2520
cgggctgaac tccaaattta cttttttctct ccgtacgtgg tctgctgcag actacgcata  2580
cactgcgtct gacgtggcag aaacaacaaa cgtacagggg tgggtctgca tataccaaat  2640
cactcacggg aaggctgaac aggacactct ggtcgtgtcg gtcagcgccg caaggactt  2700
tgaactgcgc ctcccaattg accccgcac gcaaccacc actgccgggg agtcagcaga  2760
ccctgtcacc accaccgttg agaactacgg tggtgagaca caggctcagc gacgtcagca  2820
cactgacgtc ggcttcatca tggacaggtt tgcgaaaatc agcccgtga gccccacgca  2880
```

```
cgtcattgac ctcatgcaaa cacaccaaca cgcgttggtg ggtgcccttt tgcgtgcagc   2940
cacgtactac ttctccgatc tggagattgt ggtgcgtcat gatggcaact tgacgtgggt   3000
gcccaatgga gcacctgtag aagccttggc caacacaagc aacccaccg cctaccacaa    3060
gcagccattt acgagacttg cgctcccta caccgcgccg caccgagtgt tggcaacagt    3120
gtataacgga gtaagcaagt actctacaac tggtaatgac agaagggtg acctgggcg     3180
tcttgcggcg cgggtcgccg cacagctccc cagctctttc aattttggtg caattcgggc   3240
cacgaccgtc cacgagcttc tcgtgcgcat gaaacgtgcc gagctctact gtcccaggcc   3300
tctgctggca gtgaagtgt tgtcgcagga cagacacaag caaagatca ttgcacctgc     3360
aaagcaacttt ctgaattttg acctgcttaa gctagccgga gacgttgagt ccaaccctg   3420
gcccttcttc ttctccgacg ttaggtcaaa cttttccaag ctggtagaca caatcaacca   3480
gatgcaggaa gacatgtcca caaagcacgg acctgacttt aaccggttgg tgtccgcttt   3540
tgaggagttg gccactggag tgaaagccat caggaccggt cttgacgagg ccaagccctg   3600
gtacaagctt atcaagctcc tgagccgcct gtcgtgcatg gccgctgtgg cagcacggtc   3660
aaaggaccca gtccttgtgg ccatcatgct ggctgacacc ggtctcgaga ttctggacag   3720
caccttcgtc gtgaagaaga tctccgactc gctctccagt ctcttccacg tgccggcccc   3780
cgtcttcagt ttcggagccc cgattctgtt agccgggttg gtcaaggtcg cctcgagttt   3840
cttccggtcc acgcccgaag accttgagag agcagagaaa cagctcaaag cacgtgacat   3900
caacgacattt ttcgccattc tcaagaacgg cgagtggctg gtcaaattga tccttgccat   3960
ccgcgactgg atcaaggcat ggatagcctc agaagaaaag tttgtcacca cgacagactt   4020
ggtaccttagc atccttgaaa aacagcagga cctcaacgac ccaagcaagt acaaggaagc   4080
caaggagtgg ctcgacaacg cgcgccaagc gtgtttgaag agcgggaacg tccacattgc   4140
caacctgtgc aaagtggtcg ccccggcacc cagcaggtcg agacccgagc ccgtggtcgt   4200
ttgcctccgt ggcaagtccg gtcagggcaa gagtttcctt gcaaacgtgc tcgcacaagc   4260
aatctctacc catttcactg gcaggaccga ttcagtttgg tactgcccgc ctgaccctga   4320
ccacttcgac ggttacaacc aacagactgt cgttgtgatg gacgatttgg gccagaaccc   4380
cgacggcaaa gacttcaagt acttcgccca aatggtttca acaacgggt tcatcccgcg   4440
catggcatcg cttgaggata aaggcaaacc cttcaacagt aaggtcatca tagcaaccac   4500
caacctgtac tcgggcttca ccccgaggac tatggtgtgc cctgatgcc tgaaccggag   4560
gtttcacttt gacatcgacg tgagcgccaa ggacgggtac aaaattaaca acaaattgga   4620
catcatcaaa gcacttgaag atactcacac caacccagtc gcaatgtttc agtacgactg   4680
tgcccttctc aacggcatgg ctgttgaaat gaagagaatg caacaagata tgttcaagcc   4740
tcaaccaccc cttcagaacg tgtaccaact ggttcaagag gtgattgagc gggtggagct   4800
ccacgagaag gtgtcgagcc acccgatttt caaacagatc tcaattcctt cccaaaaatc   4860
cgtgttgtac ttcctcattg agaaaggaca gcacgaggca gcaattgaat tctttgaggg   4920
catggtgcac gactccatca aggaggagct ccggccgctc atccaacaaa cctcatttgt   4980
gaaacgcgct tttaagcgcc tgaaggaaaa ctttgagatt gttgccctat gtctgaccct   5040
cctgccaaac atagtgatca tgatccgcga aactcgcaag agacagcaga tggtggacga   5100
tgcagtgagt gagtacattg agagagcaaa catcaccacc gacgacaaga ctcttgatga   5160
ggcggaaaag aaccctctgg aaaccagcgg tgccagcacc tcggcttca gagagacc     5220
tctcccaggc caaaaggcgc gtaatgacga gaactccgag cccgcccagc ctgctgaaga   5280
gcaaccacaa gctgaaggac cctacgctgg cccgatggag agaccagtta aagttaaagt   5340
gaaagcaaaa gccccggtcg ttaaggaagg accttacgg ggaccggtga agaagcctgt    5400
tgctttgaaa gtgaaagcta agaacttgat cgtcactgag agtggtgccc caccgaccga   5460
cttgcaaaag ttggtcatgg gcaacaccaa gcccgttgag ctcatccttg acgggaagac   5520
ggtagccatt tgctgtgcta ctggagtttt cggcactgct tacctcgtgc ctcgtcatct   5580
tttcgcagaa aagtacgaca agatcatgtt ggacggcaga gccatgacag atagtgacta   5640
cagagtgttt gagtttgaga ttaaagtaaa aggacagac atgctctcag acgctgcgct    5700
catggtgctc caccgtggga atcgcgtgag agacatcacg aaacactttc gtgacacagc   5760
aagaatgaag aaaggcaccc ccgtcgttgg tgtgatcaac aacgccgatg tcgggagact   5820
gatttttctct ggtgaagccc ttacctacaa ggacattgta gtgtgcatgg atggagacac   5880
catgcctggg ctctttgcct acaaagccgc aaccaaggct ggttattgcg gaggagccgt   5940
cctcgctaag gacggggctg acacgttcat cgttggcacc cactccgctg gaggcaatgg   6000
cgttggatac tgctcttgcg tttccaggtc catgcttctc aagatgaagg cacacgttga   6060
ccccgaacca caccacgagg ggttgattgt tgacaccaga gatgtggaag agcgcgttca   6120
tcgtgatgcgc aaaaccaagc ttgcacccac cgttgcgtac ggtgtgttcc gtcctgagtt   6180
cgggcctgcc gccttgtcca caaggaccc gcgcctgaac gacggtgttg tcctcgacga   6240
agtcatcttc tccaaacaca agggagacac aaagatgtct gaggaagaca aagcgctgtt   6300
ccgccgctgt gctgctgact acgcgtcacg cctgcacagc gtgttgggta cggcaaatgc   6360
cccactgagc atctacgagg caattaaagg cgttgatgga ctcgacgcaa tggaaccaga   6420
caccgcaccc ggcctcccct gggcactcca ggggaagcgc cgtggcgcgc tcatcgactt   6480
cgagaacggc actgttggac ccgaagttga ggctgccttg aagctcatgg agaaaagaga   6540
atacaagttt gcttgccaaa ccttcctgaa ggacgagatt cgcccgatgg agaaagtacg   6600
tgccggtaag actcgcattg tcgacgtcct acctgttgaa cacatcctct acaccaggat   6660
gatgattggc agattttgtg cacaaatgca ctcaaacaac gaccccaaa ttggctcggg    6720
ggtcggttgt aacccgatg ttgattggca aagatttggc acacacttcg cccaatacag    6780
aaacgtgtgg gatgtggact attcggcctt cgatgctaac cactgcagtg acgccatgaa   6840
catcatgttt gaggaagtgt ttcgcacaga attcgggttc cacccaaacg ctgagtggat   6900
cctgaagact ctccgtgaaca cggaacacgc ctatgagaac aaacgcatca ctgttgaagg   6960
cgggatgcca tctgttgtt ccgcaacaag catcatcaac acaatttga acaacatcta     7020
cgtgctctac gctttgcgta gacactatga gggagttgag ctggacactt acaccatgat   7080
ctcttacgga gacgatatcg tggtggcaag tgattacgat ttggactttg aggctctcaa   7140
gccccacttc aaatcccttg gtcaaaccat cactccagct gacaaaagcg acaaaggttt   7200
tgttcttggt cactccatta ctgatgtcac ttttcctcaa agacacttcc acatggatta   7260
tggaactggg ttttacaaa ctgatgtcct caaagacct ttgaggcta tccttctcctt     7320
tgcacgccgt gggaccatac aggagaagtt gatctccgtg gcaggactcg tcgttcactc   7380
tggaccagac gagtaccggc gtctcttcga gcccttcaa ggcctcttcg agattccaag    7440
ctacagatca cttaccctgc gttgggtgaa cgccgtgtgc ggcgacgcat aatccctcag   7500
agactacatt ggcatactgt ttctgaggcg cgcgacgccg taggagtgaa aagcctgaaa   7560
gggcttttcc cgcttcctat tccaaaaaaa aaaaaaaaa                         7600
```

```
SEQ ID NO: 25          moltype = DNA  length = 7597
FEATURE                Location/Qualifiers
misc_feature           1..7597
                       note = Fusion Nucleotide Sequence containing O1 Campos
                        strain of FMD (complete genome)
source                 1..7597
                       mol_type = other DNA
                       organism = synthetic construct
SEQUENCE: 25
ttgaaagggg gcgctagggt ctcacccta gcatgccaac gacagtcccc gcgttgcact     60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
cttcacccc ccccccccc ccccccccc cccccctaa gttctaccgt    420
cgttcccgac gtaaagggat gtaaccacaa gcttactacc gcctttcccg gcgttaaagg    480
gatgtaacca caagacttac cttcacccgg aagtaaaacg gcaacttcac acagttttgc    540
ccgtttttcat gagaaatggg acgtctgcgc acgaaacgcg ccgtcgcttg aggaggactt    600
gtacaaaaac gatctaagca ggtttcccca actgacacaa accgtgcaat ttgaaactcc    660
gcctgggctt tccaggtcta gaggggtgac actttgtgct tgtttgact ccacgttcga    720
tccactggcg agtgttagta acaacactgc tgcttcgtag cggagcatga cggccgtggg    780
accccccccc ttggtaacaa ggacccacgg ggccaaaagc cacgtccgaa tggacccgtc    840
atgtgtgcaa acccagcaca gtagcttgt tgtgaaactc actttaaagt gacattgata    900
ctggtactca agcactggtg acaggctaag gatgcccttc aggtaccccg aggtaacacg    960
tgacactcgg gatctgagaa ggggaccggg gcttctataa aagcgcccgg tttaaaaagc   1020
ttctatgtct gaataggtga ccggaggccg gcacctttct tttaattaca ctggacttat   1080
gaacacaact gattgtttta tcgctttggt acacgctatc agagagatca gagcattttt   1140
cctaccacga gccacaggaa tgggggccgg ccaatccagt ccggcgaccg gctcgcagaa   1200
ccaatctggc aacactggca gcataattaa caactactac atgcagcaat accagaactc   1260
catggacaca cagcttggtg acaacgcaat cagtggaggc tctaacgagg ctccaccga    1320
cacaacctcc acccacacaa ccaacaccca gaacaatgac tggttctcca aacttgcaag   1380
ctctgctttc agcggtcttt tcggcgctct tctcgccgac aagaagacag aggagaccac   1440
tctcctcgaa gaccgcatcc tcaccacccg taaccggccac accacgtcga caacccagtc   1500
aagcgttgga gtcacatacg ggtacgcaac agctgaggat tttgtgagcg gaccgaacac   1560
ttccggtctc gagaccagag ttgtgcaggc agaacggttt ttcaaaaccc acctcttcga   1620
ctgggtcacc agtgactcat tcggacgttg ccacctcctg gaactccccga ccgaccacaa   1680
aggtgtctac ggcagcctga ccgactcgta tgcatataga tgaaacggct gggatgctga   1740
ggtcaccgcg gttggcaacc agttcaacgg agggtgcctg ctggtcgcaa tggtaccaga   1800
gcttcgttct atccaaaaga gggaactgta ccagctcaca cttttccctc accagttcat   1860
caacccacgc acgaacatga ctgcgcacat cacagtgccc tttgttggcg tcaaccgcta   1920
cgaccagtac aaggttcaca gccttggac cctttgtgtt atggttgtag cccctctgac   1980
cgtcaacact gaaggtgccc ctcagatcaa ggtgtatgcc aacattgccc caaccaacgt   2040
gcacgtcgcg ggtgagtttc cttccaagga gggaatattc cccgtggcct gtagcgacgg   2100
ctatggtggc ctggtgacca cggacccgaa gacggctgac cccgtttatg ggaaagtgtt   2160
caaccccccc cgcaaccagt tgccgggcgc ttttaccaac ctccttgatg tggctgaggc   2220
atgcccgacg tttctgcact tcgagggtga cgtaccgtac gtgaccacga aaacagatc    2280
ggacagggtg cttgctcagt tgatatgtc tttggcagca aaacatgt caaacacctt    2340
cctcgcaggt cttgcgcagt actacacaca gtacagtggc accatcaacc tgcacttcat   2400
gttcacagga cccactgacg cgaaggcgcg ttacatgatt gcctacgccc caccaggcat   2460
ggagccgccc aagacacctg aggcggccgc gcactgcatt catgctgaat gggacactgg   2520
gttgaactca aagttactt tttccatccc ctacctctcg gccgccgatt acgcgtacac   2580
cgcgtctgac gtgccgagag ccacaaatgt gcagggatgg gtctgcttgt ttcaaattac   2640
acatggcaag gccgacgcg acgctctggt cgtactggct agtgctggta aagacttgta   2700
gctaaggctg ccggtggacg cccgtgcgga aaccacttct gcgggcgagt cagcggatcc   2760
tgtcaccgcc actgttgaaa actacggtgg cgaaacacag atccagaggc gccaacacac   2820
ggacgtctcg ttcatcatgg acagatttgt gaaagtgaca ccgcaaaacc aaattaacat   2880
tttggacctc atgcagattc catcacacac tttggtggga gcgctcctac gcgcgtccac   2940
ttactacttc tctgacttgg agatagcagt aaaaacacgag gggagacctca cctgggttcc   3000
aaatggagcg cctgaaaagg cgttggacaa caccaccaac caactgcttt accacaaggc   3060
accactcacc cggcttgccc tgccctacac cgcgccccac cgcgtgttgg caaccgtgta   3120
caacgggag tgcaggtaca gcagaaatgc tgtgccaac gtgagaggtg accttcaggt    3180
gttggctcaa aaggtggcac ggacgctgcc tacctcctcc aactacggtg ccatcaaagc   3240
gaccggggtc accgagttgc tttaccggat aagagggggcc gaaacatact gtccaaggcc   3300
cttgctggca atccacccaa ctgaagccag acacaaacag aaaattgtgg caccggtgaa   3360
acagttctga attttgacct tctcaagcta gccggagacg ttgagtccaa ccctgggccc   3420
ttcttcttct ccgacgttag gtcaaactttt tccaagctgg tagacacaat caaccagatg   3480
caggaagaca tgtccacaaa gcacggacct gactttaacc ggttggtgtc cgcttttgag   3540
gagttggcca ctgagtgaa agccatcagg accggtcttg acgaggccaa gcctggtac    3600
aagcttatca agctcctgag ccgcctgcg tgcatggccg ctgtggcagc acggtcaaag   3660
gacccagtcc ttgtggccat catgctggct gacaccggtc tcgagattct ggacagcacc   3720
ttcgtcgtga agaagatctc cgactcgctc tccagtctct tccacgtgcc ggccccgtc    3780
ttcagtttcg gagcccgat tctgttagcc gggttggtca aggtcgctc gagtttcttc   3840
cggtccacgc ccgaagacct tgagagagca gagaaacagc tcaaagcacg tgacatcaac   3900
gacattttcg ccattctcaa gaacggcgag tggctggtca aattgatcct tgccatccgc   3960
gactggatca aggcatggat agcctcagaa gaaaagtttg tcaccacgac agacttgta    4020
cctagcatcc ttgaaaaaca gcaggacctc aacgacccca gcaagtacaa ggaagccaag   4080
gagtggctcg acaacgcgcg ccaagcgtgt ttgaagagcg ggaacgtcca cattgccaac   4140
```

-continued

```
ctgtgcaaag tggtcgcccc ggcacccagc aggtcgagac ccgagcccgt ggtcgtttgc  4200
ctccgtggca agtccggtca gggcaagagt ttccttgcaa acgtgctcgc acaagcaatc  4260
tctacccatt tcactggcag gaccgattca gtttggtact gcccgcctga ccctgaccac  4320
ttcgacggtt acaaccaaca gactgtcgtt gtgatggacg atttgggcca gaaccccgac  4380
ggcaaagact tcaagtactt cgcccaaatg gtttcaacaa cggggttcat cccgcccatg  4440
gcatcgcttg aggataaagg caaacccttc aacagtaagg tcatcatagc aaccaccaac  4500
ctgtactcgg gcttcacccc gaggactatg gtgtgccctg atgccctgaa ccggaggttt  4560
cactttgaca tcgacgtgag cgccaaggac gggtacaaaa ttaacaacaa attggacatc  4620
atcaaagcac ttgaagatac tcacaccaac ccagtggcaa tgtttcagta cgactgtgcc  4680
cttctcaacg gcatggctgt tgaaatgaag agaatgcaac aagatatgtt caagcctcaa  4740
ccacccccttc agaacgtgta ccaactggtt caagaggtga ttgagcgggt ggagctccac  4800
gagaaggtgt cgagccaccc gattttcaaa cagatctcaa ttccttccca aaaatccgtg  4860
ttgtacttcc tcattgagaa aggacagcac gaggcagcaa ttgaattctt tgagggcatg  4920
gtgcacgact ccatcaagga ggagctccgg ccgctcatcc aacaaacctc atttgtgaaa  4980
cgcgctttta agcgcctgaa ggaaaacttt gagattgttg ccctatgtct gaccctcctg  5040
gccaacatag tgatcatgat ccgcgaaact cgcaagagac agaagatggt ggacgatgca  5100
gtgagtgagt acattgagag agcaaacatc accaccgacg acaagactct tgatgaggcg  5160
gaaaagaacc ctctggaaac cagcggtgcc agcaccgtcg gcttcagaga gagacctctc  5220
ccaggccaaa aggcgcgtaa tgacgagaac tccgagcccg cccagcctgc tgaagagcaa  5280
ccacaagctg aaggacccta cgctggcccg atggagagac cagttaaagt taaagtgaaa  5340
gcaaaagccc cggtcgttaa ggaaggacct tacgagggac cggtgaagaa gcctgttgct  5400
ttgaaagtga aagctaagaa cttgatcgtc actgagagtg gtgcccccacc gaccgacttg  5460
caaaagttgg tcatgggcaa caccaagccc gttgagctca tccttgacgg gaagacggta  5520
gccatttgct gtgctactgg agttttcggc actgcttacc tcgtgcctcg tcatcttttc  5580
gcagaaaagt acgacaagat catgttggac ggcagagcca tgacagatag tgactacaga  5640
gtgtttgagt ttgagattaa agtaaaagga caggacatgc tctcagacgc tgcgctcatg  5700
gtgctccacc gtgggaatcg cgtgagagac atcacgaaac actttcgtga cacagcaaga  5760
atgaagaaag gcacccccgt cgttggtgtg atcaacaacg ccgatgtcgg gagactgatt  5820
ttctctggtg aagcccttac ctacaaggac attgtagtgt gcatggatgg agacaccatg  5880
cctgggctct ttgcctacaa agccgcaacc aaggctggtt attgcggagg agccgtcctc  5940
gctaaggacg gggctgacac gttcatcgtt ggcacccact ccgctggagg caatggcgtt  6000
ggatactgct cttgcgtttc caggtccatg cttctcaaga tgaaggcaca cgttgacccc  6060
gaaccacacc acgaggggtt gattgttgac accagagatg tggaagagcg cgttcacgtg  6120
atgcgcaaaa ccaagcttgc acccaccgtt gcgtacggtg tgttccgtcc tgagttcggg  6180
cctgccgcct tgtccaacaa ggacccgcgc ctgaacgacg gtgttgtcct cgacgaagtc  6240
atcttctcca aacacaaggg agacacaaag atgtctgagg aagacaaagc gctgttccgc  6300
cgctgtgctg ctgactacgc gtcacgcctg cacagcgtgt tgggtacggc aaatgcccca  6360
ctgagcatct acgaggcaat taaaggcgtt gatggactcg acgcaatgga accagacacc  6420
gcacccggcc tcccctgggc actccagggg aagcgccgtg gcgcgctcat cgacttcgag  6480
aacggcactg ttggacccga agttgaggct gccttgaagc tcatggagaa aagagaatac  6540
aagtttgctt gccaaacctt cctgaaggac gagattcgcc cgatggagaa agtacgtgcc  6600
ggtaagactc gcattgtcga cgtcctacct gttgaacaca tcctctacac caggatgatg  6660
attggcagat tttgtgcaca aatgcactca aacaacggac cccaaattgg ctcggcggtc  6720
ggttgtaacc ctgatgttga ttggcaaaga tttggcacac acttcgccca atacagaaac  6780
gtgtgggatg tggactattc ggccttcgat gctaaccact gcagtgacgc catgaacatc  6840
atgtttgagg aagtgtttcg cacagaattc gggttccacc caaacgctga gtggatcctg  6900
aagactctcg tgaacacgga acacgcctat gagaacaaac gcatcactgt tgaaggcggg  6960
atgccatctg gttgttccgc aacaagcatc atcaacacaa ttttgaacaa catctacgtg  7020
ctctacgctt tgcgtagaca ctatgaggga gttgagctgg acacttacac catgatctct  7080
tacggagacg atatcgtggt ggcaagtgat tacgatttgg actttgaggc tctcaagccc  7140
cacttcaaat cccttggtca aaccatcact ccagctgaca aaagcgacaa aggttttgtt  7200
cttggtcact ccattactga tgtcactttc ctcaaaagac acttccacat ggattatgga  7260
actgggtttt acaaacctgt gatggcctca aagacccttg aggctatcct ctcctttgca  7320
cgccgtggga ccatacagga gaagttgatc tccgtggcag gactcgctgt tcactctgga  7380
ccagacgagt accggcgtct cttcgagccc tttcaaggcc tcttcgagat tccaagctac  7440
agatcacttt acctgcgttg ggtgaacgcc gtgtgcggcg acgcataatc cctcagagac  7500
tacattggca tactgtttct gaggcgcgcg acgccgtagg agtgaaaagc ctgaaagggc  7560
ttttcccgct tcctattcca aaaaaaaaaa aaaaaaa                          7597

SEQ ID NO: 26           moltype = DNA  length = 7586
FEATURE                 Location/Qualifiers
misc_feature            1..7586
                        note = Fusion Nucleotide Sequence containing C3 Indaial
                         strain of FMD (complete genome)
source                  1..7586
                        mol_type = other DNA
                        organism = synthetic construct
SEQUENCE: 26
ttgaaagggg gcgctagggt ctcacccccta gcatgccaac gacagtcccc gcgttgcact  60
ccacactcac gttgtgcgtg cgcggagctc gatggactat cgttcaccca cctacagctg  120
gactcacggc accgtgtggc cacttggctg gattgtgcgg acgaacaccg cttgcgcttc  180
tcgcgtgacc ggttagtact ctcaccacct tccgcccact tggttgttag cgctgtcttg  240
ggcactcctg ttgggggccg ttcgacgctc cgcgagtttc cccgcacggc aactacggtg  300
atggggccgt accgcgcggg ctgatcgcct ggtgtgcttc ggctgtcacc cgaagcctac  360
ctttcacccc cccccccccc cccccccccc cccccccccc cccccctaa gttctaccgt  420
cgttcccgac gtaaagggat gtaaccacaa gcttactacc gcctttcccg gcgttaaagg  480
gatgtaacca caagacttac cttcacccgg aagtaaaacg gcaacttcac acagttttgc  540
ccgttttcat gagaaatggg acgtctgcgc acgaaacgcg ccgtcgcttg aggaggactt  600
gtacaaacac gatctaagca ggtttcccca actgacacaa accgtgcaat ttgaaactcc  660
```

```
gcctgggctt tccaggtcta gaggggtgac actttgtact gtgtttgact ccacgttcga  720
tccactggcg agtgttagta acaacactgc tgcttcgtag cggagcatga cggccgtggg  780
accccccccc ttggtaacaa ggacccacgg ggccaaaagc cacgtccgaa tggaccgtc   840
atgtgtgcaa acccagcaca gtagctttgt tgtgaaactc actttaaagt gacattgata  900
ctggtactca agcactggtg acaggctaag gatgcccttc aggtacccg  aggtaacacg   960
tgacactcgg gatctgagaa ggggaccggg gcttctataa aagcgccgg  tttaaaaagc  1020
ttctatgtct gaataggtga ccggaggccg gcacctttct tttaattaca ctggacttat  1080
gaacacaact gattgtttta tcgctttggt acacgctatc agagagatca gagcattttt  1140
cctaccacga gccacaggaa tgggaccgg  acaatccagc ccggcgactg gctcgcagaa  1200
ccaatctggc aacactggta gcataatcaa caactactac atgcaacagt accaaaattc  1260
catggacaca cagctgggtg acaatgctat tagtggtggc tccaacgagg gctccacaga  1320
tacaacttcc acccacacaa ccaacactca aaacaacgac tggttttcca aactcgccag  1380
ttctgccttt agcggtcttt tcggtgctct tcttgccgac aagaagaccg aggaaaccac  1440
actacttgaa gaccgcatcc tcaccacccg caacgtcga  caactcagtc             1500
gagcgttggg gtcacatacg ggtacgcaac aactgaggat agcacgtcag ggcccaacac  1560
atccggcctt gagacacgtg ttcaccaggc agaacggttt ttcaagatga cactctttga  1620
atgggttccc tcccagagtt ttggacacat gcacaaggtc gttctgccct cagaaccgaa  1680
aggtgtctat gggggtctcg tcaagtcata cgcgtacatg cgcaatggct gggacgttga  1740
ggtgactgct gttggaaacc agttcaacg  cggttgtctc ctggtggcgc tcgttcctga  1800
aatgggtgac atcagtgaca gagagaagta ccaactgact ctctacccccc accaattcat  1860
caacccacgc actaacatga cggcacacat caccgtgcct tacgtgggtg tcaacagata  1920
cgaccaatac aaccaacaca agccctggac tcttgtcgtc atggtcgttg ctccacttac  1980
tgtgaacaca tcaggtgccc agcagatcaa ggtgtatgcc aacatagccc caaccaacgt  2040
tcacgttgct ggtgaacttc cctcaagga  ggggatcttc cccgttcgt  gtgccgacgg  2100
ctatggcaac atggtgacaa ctgacccgaa gacagctgac cctgcctacg gaaagtcta   2160
caatccaccc aggaccgccc tgccgggccg gttcacaaac tacctggatg ttgctgaggc  2220
ttgccccact ctcctgacgt tcgagaacgt gccttacgtt tcaacacgga ctgatgaca   2280
aaggctgttg gccaagttcg acgtgtcatt ggcagcgaaa cacatgtcaa acacttactt  2340
ggctggcttg gcccagtact acacacagta cgctgggaca atcaacctgc acttcatgtt  2400
cactgggcca accgacgcga aagctcggta catggtggca tacgtgcccc ctggcatgga  2460
agcaccagac aacccagagg aggctgccca ctgcatacac gcagagtggg  acactggttt  2520
gaactctaag ttcacatttt caatcccgta catctcggcc gctgactacg catacaccgc  2580
gtccagcgag gctgaaacaa caagcgtaca gggatgggtt tgtgtgtacc agatcactca  2640
cggcaaggca gacgctgacg cgctcgtcgt ctccgcttcg gcggggaaag actttgagct  2700
ccggctacct gtggacgcta gacagcaaac tacgaccact ggcgaatctg ccgacccgt   2760
caccactacc gttgagaact acggaggaga aacacaaact caacgtcgcc accacactga  2820
cgttgccttc gttcttgacc ggtttgtgaa ggtccaggtg tcgggcaacc aacacacact  2880
ggacgttatg caggtacaca aggacagtat tgtgggtgca ctcctacgcg cagccacata  2940
ctacttctct gacttggaaa tagcagtgac tcacactggg aagctcacat gggtgcccaa  3000
cggcgcccca gtttctgcac ttgacaacac aaccaacccc actgcctacc acaaggggcc  3060
gctgactcgg ctggctctcc catacaccgc accacaccgc gtgctggcca cggcgtacac  3120
cggtacaacg gcctacacta ccggtgtacg caggggagac ctagcccact ggcggcggc   3180
gcacgctcgg cacctgccga cgtcgttcaa ctttggtgca gttaaagcag agacaatcac  3240
agagctgctt gtgcgcatga agcgtgctga actctactgc cccagaccgg tccttccggt  3300
ccaaccagcg ggcgataggc acaaacaacc gctcattgcg ccagcgaaac agcttctgaa  3360
ttttgacctg cttaagctag ccggagacgt tgagtccaac cctgggccct tcttcttctc  3420
cgacgttagg tcaaactttt ccaagctggt agacacaatc aaccagatgc aggaagacat  3480
gtccacaaag cacggacctg actttaaccg gttggtgtcc gcttttgagg agttggccac  3540
tggagtgaaa gccatcagga ccggtcttga cgaggcaag  ccctggtaca agcttatcaa  3600
gctcctgagc cgcctgtcgt gcatggccgc tgtggcagca cggtcaaagg acccagtcct  3660
tgtgccatc  atgctggctg acaccggtct cgagattctg gacagcacct tcgtcgtgaa  3720
gaagatctcc gactcgctct ccagtctctt ccacgtgccg gccccgtct  tcagtttcgg  3780
agccccgatt ctgttagccg ggttggtcaa ggtcgcctcg agtttcttcc ggtccacgcc  3840
cgaagacctt gagagagcag agaaacagct caaagcacgt gacatcaacg acattttcgc  3900
cattctcaag aacggcgagt ggctgtcaa  attgatcctt ccatccgcg  actgaatcaa  3960
ggcatggata gcctcagaag aaaagtttgt caccacgaca gacttggtac ctagcatcct  4020
tgaaaaacag caggacctca acgacccaag caagtacaag gaagccaagg agtggctcga  4080
caacgcgcgc caagcgtgtt tgaagagcgg gaacgtccac attgccaacc tgtgcaaagt  4140
ggtcgcccg  gcaccagca ggtcgagacc cgagcccgtg gtcgtttgcc tccgtggcaa  4200
gtccggtcag ggcaagagtt tccttgcaaa cgtgctcgca caagcaatct ctacccattt  4260
cactggcagg accgattcag tttggtactg cccgcctgac cctgaccact tcgacggtta  4320
caaccaacag actgtcgttg tgatggacga tttgggccag aaccccgacg gcaaagactt  4380
caagtacttc gcccaaatgg tttcaacaac ggggttcatc ccgcccatgg catcgcttga  4440
ggataaaggc aaacccttca acagtaaggt catcatagca accaccaacc tgtactcgga  4500
cttcacccgg aggactatgg tgtgccctga tgcctgaaac cggaggttc  actttgacat  4560
cgacgtgagc gccaaggacg ggtacaaaat taacaacaaa ttggacatca tcaaagcact  4620
tgaagatact cacaccaacc cagtggcaat gtttcagtac gactgtgccc ttctcaacgg  4680
catggctgtt gaaatgaaga aatgcaacaa agatatgttc aagcctcaac caccccttca  4740
gaacgtgtac caactggttc aagaggtgat tgagcgggtg gagctccacg agaaggtgtc  4800
gagccacccg attttcaaac agatctcaat tccttcccaa aaatccgtgt tgtacttcct  4860
cattgagaaa ggacagcacg aggcagcaat tgaattcttt ggagcatgg  tgcacgactc  4920
catcaaggag gagctccggc cgctcatcca acaaacctca tttgtgaaac gcgctttaa   4980
gcgcctgaag gaaaactttg agattgttgc cctatgtctg accctcctgg ccaacatagt  5040
gatcatgatc cgcgaaactc gcaagagaca gaagatggtg gacgatgcag tgagtgagta  5100
cattgagaga gcaaacatca ccaccgacga caagactctt gatgaggcgg aaaagaaccc  5160
tctgaaaacc agcggtgcca gcaccgtcgg cttcagagag agacctctcc caggccaaaa  5220
ggcgcgtaat gacgagaact ccgagcccgc ccagcctgct gaagagcaac acaagctgaa  5280
aggaccctac gctggcccga tggagagacc agttaaagtt aaagtgaaag caaaagcccc  5340
ggtcgttaag gaaggacctt acgagggacc ggtgaagaag cctgttgctt tgaaagtgaa  5400
```

```
agctaagaac ttgatcgtca ctgagagtgg tgccccaccg accgacttgc aaaagttggt  5460
catgggcaac accaagcccg ttgagctcat ccttgacggg aagacggtag ccatttgctg  5520
tgctactgga gttttcggca ctgcttacct cgtgcctcgt catcttttcg cagaaaagta  5580
cgacaagatc atgttggacg gcagagccat gacagatagt gactacgag tgtttgagtt  5640
tgagattaaa gtaaaaggac aggacatgct ctcagacgct gcgctcatgg tgctccaccg  5700
tgggaatcgc gtgagagaca tcacgaaaca ctttcgtgac acagcaagaa tgaagaaagg  5760
caccccgtc gttggtgtga tcaacaacgc cgatgtcggg agactgattt tctctggtga  5820
agcccttacc tacaaggaca ttgtagtgtg catggatgga gacaccatgc ctgggctctt  5880
tgcctacaaa gccgcaacca aggctggtta ttgcggagga gccgtcctcg ctaaggacgg  5940
ggctgacacg ttcatcgttg gcacccactc cgctgggagc aatgcgttg gatactgctc  6000
ttgcgtttcc aggtccatgc ttctcaagat gaaggcacac gttgaccccg aaccacacca  6060
cgaggggttg attgttgaca ccagagatgt ggaagagcgc gttcacgtga tgcgcaaaac  6120
caagcttgca cccaccgttg cgtacggtgt gttccgtcct gagttcgggc ctgccgcctt  6180
gtccaacaag gacccgcgcc tgaacacggg tgttgtcctc gacgaagtca tcttctccaa  6240
acacaaggga gacacaaaga tgtctgagga agacaaagcg ctgttccgcc gctgtgctgc  6300
tgactacgcg tcacgcctgc acagcgtgtt gggtacggca aatgcccac tgagcatcta  6360
cgaggcaatt aaaggcgttg atggactcga cgcaatggaa ccagacaccg cacccggcct  6420
ccctgggca ctccagggga gcgccgtgg cgcgctcatc gacttcgaga acggcactgt  6480
tggacccgaa gttgaggctg ccttgaagct catggagaaa agaatacaa agtttgcttg  6540
ccaaaccttc ctgaaggacg agattcgccc gatggagaaa gtacgtgccg gtaagactcg  6600
cattgtcgac gtcctacctg ttgaacacat cctctacacc aggatgatga ttggcagatt  6660
ttgtgcacaa atgcactcaa acaacgacc ccaaattggc tcggcggtcg gttgtaaccc  6720
tgatgttgat tggcaaagat ttggcacaca cttcgcccaa tacagaaacg tgtgggatgt  6780
ggactattcg gccttcgatg ctaaccactg cagtgacgcc atgaacatca tgtttgagga  6840
agtgtttcgc acagaattcg ggttccaccc aaacgctgag tggatcctga gactctcgt  6900
gaacacggaa cacgcctatg agaacaaacg catcactgtt gaaggcggga tgcatctgg  6960
ttgttccgca acaagcatca tcaacacaat tttgaacaac atctacgtgc tctacgcttt  7020
gcgtagacac tatgagggag ttgagctgga cacttacacc atgatctctt acggagacga  7080
tatcgtggtg gcaagtgatt acgatttgga ctttgaggct ctcaagcccc acttcaaatc  7140
ccttggtcaa accatcactc cagctgacaa aagcgacaaa ggttttgttc ttggtcactc  7200
cattactgat gtcactttcc tcaaaagaca cttccacatg gattatgaa ctgggtttta  7260
caaacctgtg atggcctcaa agaccttga ggctatcctc tcctttgcac gccgtgggac  7320
catacaggag aagttgatct ccgtggcagg actcgctgtt cactctggac cagacgagta  7380
ccggcgtctc ttcgagccct tcaaggcct cttcgagatt ccaagctaca gatcacttta  7440
cctgcgttgg gtgaacgccg tgtgcgcga cgcataatcc ctcagagact acattggcat  7500
actgtttctg aggcgcgcga cgccgtagga gtgaaaagcc tgaaagggct tttcccgctt  7560
cctattccaa aaaaaaaaaa aaaaaa                                       7586
```

SEQ ID NO: 27          moltype = DNA   length = 2076
FEATURE                Location/Qualifiers
misc_feature           1..2076
                       note = Fusion Nucleotide Sequence containing capsid and 2A
                        partial sequence of C3 Indaial strain of FMD
source                 1..2076
                       mol_type = other DNA
                       organism = synthetic construct
SEQUENCE: 27
```
ggggccggcc aatccagccc agctactggc tcgcagaacc aatctggtaa cacaggtagc   60
ataatcaaca actactacat gcaacagtac caaaactcca tggacacaca gcttggtgac  120
aatgccatca gtgaggctc taacgagggc tccacggaca caacttcaac tcacacaacc  180
aacacccaaa acaatgactg gttttcaaga ctcgccgatt cggccttctc cggtttgttt  240
ggggccttgc ttgccgacaa gaagacggag gagacgacac tccttgagga ccgcattctc  300
accactcgca atgggcacac cacctccacg acccagtcca gcgtaggcgt tacatacggg  360
tactccacaa cagaggacca cgttgctgga cccaacacat caggtttgga gacacgagtg  420
gtacaggcag agagattcta caaaaagttt ttgtttgatt ggacaacgga caagccttct  480
ggacacctgc acaaactgga gttgcccacc gaccaccacg tgttttcgg acacttggtg  540
gactcatacg cctacatgag gaacggttgg gacgttgagg tgtctgctgt tggcaaccag  600
ttcaacggcg gatgcctcct agtggccatg gtacccgaat ggaagagtt tgaaacgcgg  660
gagaagtacc agctcacgct ttttccgcac cagttcatta gcccagaac caacatgacc  720
gcccacatca cggttcctta ccttggtgtg aatagatatg atcagtacaa aaacacaaa  780
ccctggacac tggttgtcat ggtcgtgtcc ccgctcacgg tcaacgccac gagcgcggca  840
cagatcaagg tctatgccaa catcgctccg acctacgttc atgtgccgg cgagctcccc  900
tcgaaagagg ggatcttccc tgtcgcgtgc gcggacggtt acgaggact ggtgacaacg  960
gacccgaaaa cagctgaccc cgcctacggc aaggtgtaca atccggccg gactaactac 1020
cccgggcgtt tcactaactt gttggacgtg gctgaggcat gtcccacctt tctgtgtttt 1080
gacgacggga aaccgtacgt taccacacag acaggtgagt ctcgtcttct ggccaagttc 1140
gacctttccc ttgccgcgaa gcacatgtct aacacatact tggcaggaat gcccagtac 1200
tacacacagt actcaggcac catcaatttg catttcatgt tcacaggttc aactgattca 1260
aaagcccgct acatggtggc ttacatcccg cctggggtgg aaacaccacc ggacacacct 1320
gagagggcag cccactgcat cctatgctgag tgggacacag gctgaattc caaattcaca 1380
ttctcaatcc cgtacgtgtc tgccgcggat tacgcctaca cggcgtctga tgaggcagag 1440
acaacaaacg tacagggatg gtctgcgtt taccagatca cacgggaa ggctgacaac 1500
gacactctgtg tcgtgtcggt tagcgccggc aaggacttcg agttgcgcct cccattgac 1560
ccccgaccgc agaccaccgc tactgggaa tcagcagcc ctgtcaccac cactgtagag 1620
aactacggcg gtgagacaca agttcagaga cgccaccaca ccgacgttgg cttcatcatg 1680
gacagatttg tgaaaataaa cagcccaaaa tccacccatg ttattgacct catgcaaacc 1740
caccaacacg gtcagtggg tgcgctgctg cgtgcggcga cctactactt ctcagatctg 1800
gaaattgttg tgcggcatga cggcaaccta acttgggtgc caatggtgc tcccgtgtca 1860
gccttgtcca acaccagcaa ccccaccgcc tacaacaagg caccgttcac gagacttgcc 1920
```

```
ctccoctaca ccgcgccaca ccgcgtgttg gcgactgtgt acaacgggac gagcaagtac   1980
actgtgagtg ggtcaagcag acgaggcgac ttggggttccc tcgcggcacg agtcgtgaag  2040
gcacttcctg cttctttcaa ctacggtgca atcaag                             2076

SEQ ID NO: 28           moltype = DNA  length = 23
FEATURE                 Location/Qualifiers
misc_feature            1..23
                        note = Primer
source                  1..23
                        mol_type = other DNA
                        organism = synthetic construct
SEQUENCE: 28
gacaaaggtt ttgttcttgg tca                                           23

SEQ ID NO: 29           moltype = DNA  length = 18
FEATURE                 Location/Qualifiers
misc_feature            1..18
                        note = Primer
source                  1..18
                        mol_type = other DNA
                        organism = synthetic construct
SEQUENCE: 29
tgcgagtcct gccacgga                                                 18

SEQ ID NO: 30           moltype = DNA  length = 20
FEATURE                 Location/Qualifiers
misc_feature            1..20
                        note = Probe
source                  1..20
                        mol_type = other DNA
                        organism = synthetic construct
SEQUENCE: 30
tcctttgcac gccgtgggac                                               20
```

FOOT-AND-MOUTH DISEASE VACCINE

CROSS REFERENCE TO RELATED APPLICATIONS

This application is a continuation of U.S. application Ser. No. 17/180,223 filed on Feb. 19, 2021, issued as U.S. Pat. No. 11,865,171, which is a continuation of U.S. application Ser. No. 16/374,105 filed on Apr. 3, 2019, issued as U.S. Pat. No. 10,967,058, which is a continuation of U.S. application Ser. No. 15/543,630 filed on Jul. 14, 2017, issued as U.S. Pat. No. 10,478,487, which is the National Stage of International Application No. PCT/US2016/013587, filed on Jan. 15, 2016, which application claims the benefit of U.S. Provisional Application No. 62/104,314, filed Jan. 16, 2015.

THE NAMES OF THE PARTIES TO A JOINT RESEARCH AGREEMENT

The claimed invention was made as a result of activities undertaken within the scope of a joint research agreement between Zoetis LLC and the United States Department of Agriculture, Agricultural Research Service.

SEQUENCE LISTING INFORMATION

The instant application contains a Sequence Listing which has been submitted electronically in XML file format and is hereby incorporated by reference in its entirety. Said XML copy, created on Nov. 15, 2023, is named ZP000077D.XML and is 95,757 bytes in size.

BACKGROUND

Foot and mouth disease (FMD) is an extremely contagious viral disease of cloven-hoofed ungulates which include domestic animals (cattle, pigs, sheep, goats, and others) and a variety of wild animals. The most prominent disease symptoms in FMDV-infected cattle include vesicular lesions of the epithelium of the mouth, tongue, teats and feet. Although some countries, among them United States, Canada, Mexico, Australia and most of Europe, are considered to be free of FMD, the disease is distributed worldwide and has a great economic impact on the export industry. Indeed, several economically devastating outbreaks have occurred over the past decade on almost every continent.

Currently killed-antigen FMDV vaccines are necessarily produced in expensive biological containment facilities, by growing large volumes (thousands of liters) of virulent FMDV that has been adapted to grow in cells, which can be sometimes difficult. This process has resulted in escape of virulent virus from the manufacturing facility causing costly outbreaks in livestock (see Cottam et al. 2008. PLOS Pathogen 4:1-8). After growth, virus is then inactivated using chemicals and antigen concentrates are prepared, followed by purification steps required to remove contaminant proteins. It is difficult to differentiate infected from vaccinated animals (DIVA) through serological diagnostic tests. There is little to no cross protection across serotypes and subtypes requiring the appropriate matching between vaccine and circulating field strains to achieve protection. Despite these shortcomings of the vaccines, billions of doses are manufactured every year around the world. Their use has been the basis for eradicating FMDV from Europe and for controlling the disease in many parts of the world through mass vaccination campaigns. Creation of genetically engineered viruses containing a backbone and suitable restriction sites partially addresses the shortcomings of inactivated vaccines as restriction sites provide loci for introduction of capsid proteins of different FMD strains. Nevertheless, the cost of antigen is the greatest contributor to the cost of FMD and most other vaccines.

The problem of FMD control is further exacerbated by the phenomenon of virus persistence. Briefly, historically, inactivated FMD vaccines have been unable to prevent persistence or carrier state (defined as virus shedding past 28 days following infection and/or exposure). Shedding animals, while not exhibiting any FMD symptoms, could remain a source of FMD infection to other animals. As such, commonly accepted disease control practices require slaughter of all animals in a vaccinated herd even if they do not have clinical signs of disease.

As such, methods and compositions which lead to vaccines with a lower antigen load without compromising efficiency and/or reducing or eliminating FMD persistence are still desired.

SUMMARY OF THE INVENTION

In one aspect, the invention provides an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide, and at least one of a polycationic polymer; a source of aluminum; and the antigen component comprises a FMD antigen composition in the amount equivalent to 0.5-8 µg of FMD virus per dose.

In certain embodiments, the immunostimulatory oligonucleotide is a CpG containing oligonucleotide. In certain embodiments, the polycationic polymer is DEAE dextran.

In different embodiments, the antigen is an FMD virus composition, and is present in the amount of 0.5-4 µg per dose, or 0.5-2 µg per dose, or 0.5-1 µg per dose, or in the amount of about 0.5 µg per dose.

The FMD virus may be inactivated or attenuated. In certain embodiments, the FMD virus is an inactivated FMD A24 Cruzeiro strain. In selected embodiments, the inactivated strain is a genetically engineered strain which contains a deletion of the leader coding region (LL) and optionally, contains negative antigenic markers.

In certain embodiments, the genetically engineered virus contains capsid proteins from a heterologous strain.

In another aspect, the invention provides a method of preventing FMD in an animal in need thereof, the method comprising administering the immunogenic composition according to the embodiments of the previous aspect to said animal. In different embodiments, the animal is selected from bovines, ovines, porcines, and caprines.

In another aspect, the invention provides a method of reducing frequency of FMD persistence in a ruminant infected with FMD comprising administering to said ruminant prior to the infection an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose.

In yet another aspect, the invention provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are not slaughtered.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are quarantined for 0-62 days.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are moved beyond the infected zone.

BRIEF DESCRIPTION OF THE DRAWINGS

FIG. 1 illustrates the difference in quality between the PEG precipitated and hollow fiber concentrated antigens.

DETAILED DESCRIPTION

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means any substance that increases the humoral or cellular immune response to an antigen. Adjuvants are generally used to accomplish two objectives: the controlled release of antigens from the injection site, and the stimulation of the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that is recognized by the animal's immune system and generates an immune response. The term includes killed, inactivated, attenuated, or modified live bacteria, viruses, or parasites. The term "antigen" also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Consisting essentially" as applied to the adjuvant formulations refers to formulation which does not contain unrecited additional adjuvanting or immunomodulating agents in the amounts at which said agent exert measurable adjuvanting or immunomodulating effects.

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

The term "emulsifier" is used broadly in the instant disclosure. It includes substances generally accepted as emulsifiers, e.g., different products of TWEEN® or SPAN® product lines (fatty acid esters of polyethoxylated sorbitol and fatty-acid-substituted sorbitan surfactants, respectively), and different solubility enhancers such as PEG-40 Castor Oil or another PEGylated hydrogenated oil.

"Humoral immune response" refers to one that is mediated by antibodies.

"Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus an immunogenic composition would be any composition that induces an immune response.

"Infected Premises" refers to premises where presumptive positive case or confirmed positive case exists based on laboratory results, compatible clinical signs, FMD case definition, and international standards.

"Infected Zone" refers to an area within 3 km beyond perimeters of presumptive or confirmed Infected Premises.

"Lipids" refers to any of a group of organic compounds, including the fats, oils, waxes, sterols, and triglycerides that are insoluble in water but soluble in nonpolar organic solvents, are oily to the touch, and together with carbohydrates and proteins constitute the principal structural material of living cells.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual, p. 25-46 (1996).

Persistently infected or carrier animals are animals shedding FMD virus past 28 days post infection or onset of clinical disease.

Adjuvant Formulations and Methods of Making

The instant application discloses several adjuvant formulations suitable for the instant invention. The common feature of these adjuvants is the presence of oil and one or more emulsifiers, wherein the oily phase comprises at least 50% of the vaccine composition encompassing the adjuvant formulations disclosed therein.

Multiple oils and combinations thereof are suitable for use of the instant invention. These oils include, without limitations, animal oils, vegetable oils, as well as non-metabolizable oils. Non-limiting examples of vegetable oils suitable in the instant invention are corn oil, peanut oil, soybean oil, coconut oil, and olive oil. A non-limiting example of an animal oil is squalane. Suitable non-limiting examples of non-metabolizable oils include light mineral oil, straight chained or branched saturated oils, and the like.

In a set of embodiments, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.) or USB Corporation (Cleveland, Ohio). Preferred mineral oil is light mineral oil commercially available under the name DRAKEOL®.

In certain embodiments particularly suitable for preventing or eliminating FMD persistence, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80, etc.), if any such emulsifiers are present. The volume of the oily phase is calculated as a sum of volumes of the oil and the emulsifier(s). Thus, for example, if the volume of the oil is 40% and the volume of the emulsifier(s) is 12% of a composition, then the oily phase would be present at 52% v/v of the composition. Similarly, if the oil is present in the amount of about 45% and the emulsifier(s) is present in the amount of about 6% of a composition, then the oily phase is present at about 51% v/v of the composition.

It also should be understood that since the adjuvants of the instant invention form only a part of the vaccines of the instant invention, the oily phase is present in an amount from 50% to 95% by volume; preferably, in an amount of greater than 50% to 85%; more preferably, in an amount from 50% to 60%, and more preferably in the amount of 50-52% v/v of each of the adjuvants of the instant invention.

In a subset of embodiments, the volume percentage of the oil and the oil-soluble emulsifier together is at least 50%, e.g., 50% to 95% by volume; preferably, in an amount of greater than 50% to 85%; more preferably, in an amount from 50% to 60%, and more preferably in the amount of 50-52% v/v of the vaccine composition. Thus, for example and without limitations, the oil may be present in the amount of 45% and the lipid-soluble emulsifier would be present in the amount of greater than 5% v/v. Thus, the volume percentage of the oil and the oil-soluble emulsifier together would be at least 50%.

In yet another subset, applicable to all vaccines of the invention, volume percentage of the oil is over 40%, e.g., 40% to 90% by volume; 40% to 85%; 43% to 60%, 44-50% v/v of the vaccine composition.

Emulsifiers suitable for use in the present emulsions include natural biologically compatible emulsifiers and non-natural synthetic surfactants. Biologically compatible emulsifiers include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

In additional embodiments, the emulsifiers used herein do not include lecithin, or use lecithin in an amount which is not immunologically effective.

Non-natural, synthetic emulsifiers suitable for use in the adjuvant formulations of the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®);

polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate).

Generally speaking, the emulsifier(s) may be present in the vaccine composition in an amount of 0.01% to 40% by volume, preferably, 0.1% to 15%, more preferably 2% to 10%. Additional ingredients present in the instant adjuvant formulations include cationic carriers, immunostimulatory oligonucleotides, monophospholipid A and analogs thereof (MPL-A), Polyinosinic:polycytidylic acid (poly:C), saponins, quaternary ammoniums, sterols, glycolipids, a source of aluminum (e.g., REHYDRAGEL® or VAC 20® wet gel) and combinations thereof.

Suitable cationic carriers include, without limitations, dextran, dextran DEAE (and derivatives thereof), PEGs, guar gums, chitosan derivatives, polycellulose derivatives like hydroxyethyl cellulose (HEC) polyethylenimene, poly aminos like polylysine and the like.

Suitable immunostimulatory oligonucleotides include ODN (DNA-based), ORN (RNA-based) oligonucleotides, or chimeric ODN-ORN structures, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used.

CpG oligonucleotides are a recently described class of pharmacotherapeutic agents that are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In selected embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligonucleotides characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-methylation, modification with proynyl-dU, inosine modification, 2-bromovinyl attachment (preferably to uridine).

The P-class immunostimulatory oligonucleotides may also contain a modified internucleotide linkage including, without limitations, phosphodiesther linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostimulatory oligonucleotides are provided below ("*" refers to a phosphorothioate bond and "-" refers to a phosphodiester bond).

SEQ ID NO: 1
5' T*C-G*T*C-G*A*C-G*A*T*C-G*G*C*G*C-G*C*G*C*C*G 3'

SEQ ID NO: 2
5' T*C-G*A*C*G*T*C*G*A*T*C*G*G*C*G*C*G*C*G*C*C*G 3'

SEQ ID NO: 3
5' T*C*G*A*C*G*T*C*G*A*T*C*G*G*C*G*C*G*C*G*C*C*G*T 3'

SEQ ID NO: 4
5' JU*C-G*A*C*G*T*C*G*A*T*C*G*G*C*G*C*G*C*G*C*C*G 3'

SEQ ID NO: 5
5' JU*C-G*A*C*G*T*C*G*A*T*C*G*G*C*G*C*G*C*G*C*C*G*T 3'

SEQ ID NO: 6
5' JU*C*G*A*C*G*T*C*G*A*T*C*G*G*C*G*C*G*C*G*C*C*G*T 3'

SEQ ID NO: 7
5' EU*C-G*A*C*G*T*C*G*A*T*C*G*G*C*G*C*G*C*G*C*C*G 3'

SEQ ID NO: 8
5' JU*C-G*T*C*G*A*C*G*A*T*C*G*G*C*G*C*G*C*G*C*C*G*T 3'

SEQ ID NO: 9
5' JU*C*G*T*C*G*A*C*G*A*T*C*G*G*C*G*C*G*C*G*C*C*G*T 3'

SEQ ID NO: 10
5' T*C-G*T*C-G*A*C-G*A*T*C-G*G*C*G*C-G*C*G*C*C*G 3'

-continued

SEQ ID NO: 11
5'-UUGUUGUUGUUGUUGUUGUU-3'

SEQ ID NO: 12
5'-UUAUUAUUAUUAUUAUUAUU-3'

SEQ ID NO: 13
5'-AAACGCUCAGCCAAAGCAG-3'

SEQ ID NO: 14
dTdCdGdTdCdGdTdTdTdTrGrUrUrGrUrGrUdTdTdT-3'

The amount of P-class immunostimulatory oligonucleotide for use in the adjuvant compositions depends upon the nature of the P-class immunostimulatory oligonucleotide used and the intended species.

In addition to the oil and the emulsifier(s), the adjuvant formulations also comprise (or consist essentially of, or consist of) a combination of an immunostimulatory oligonucleotide and a polycationic carrier. These adjuvants are referred to as "TXO".

In a set of embodiments, the TXO adjuvants may also include a source of aluminum, such as Al(OH)$_3$ gel. The TXO adjuvants with aluminum are referred to as "TXO-A".

In a set of embodiments, adjuvants TXO and TXO-A may optionally contain a sterol, such as, for example, cholesterol, lanosterol, sigmasterol, etc. TXO and TXO-A adjuvants containing the sterol are referred to as TCXO and TCXO-A, respectively. The optionally present sterol may be present in the amount of up to about 1000 µg (e.g., 100-1000 µg, 200-1000 µg, 250-700 µg, or about 400-500 µg) per dose.

In a set of embodiments, in TXO adjuvants, the immunostimulatory oligonucleotide, preferably an ODN, preferably containing a palindromic sequence, and optionally with a modified backbone, may be present in the amount of 5-400 µg per dose, and the polycationic carrier may be present in the amount of 5-400 mg per dose.

For example, in certain embodiments, one dose of TXO would comprise between about 5 and 400 µg per dose (e.g., 6.25-200 µg or 6.25-100 µg or 6.25-50 µg or 6.25-25 µg or 6.25-10 µg or 10-200 µg or 25-200 µg or 25-100 µg or 25-50 µg or 25-100 µg or 50-100 µg per dose) of the immunostimulatory oligonucleotide, and the polycationic carrier may be present in the amount of between about 5 and about 500 mg per dose (e.g., 6.25-200 mg or 6.25-100 mg or 6.25-50 mg or 6.25-25 mg or 6.25-10 mg or 10-200 mg or 25-200 mg or 25-100 mg or 25-50 mg or 25-100 mg or 50-100 mg per dose).

In certain embodiments, TXO adjuvants are prepared as follows:
  a) Sorbitan monooleate is dissolved in light mineral oil. The resulting oil solution is sterile filtered;
  b) The immunostimulatory oligonucleotide, Dextran DEAE and Polyoxyethylene (20) sorbitan monooleate are dissolved in aqueous phase, thus forming the aqueous solution; and
  c) The aqueous solution is added to the oil solution under continuous homogenization thus forming the adjuvant formulation TXO.

In a set of embodiments, in TXO-A adjuvants, the immunostimulatory oligonucleotide is present as in the TXO adjuvant, the source of aluminum is present in the amount of up to 40% v/v (e.g., 35%, 30%, 25%, 20%, 15%, 10%, 5%, 1%). In a set of embodiments, the source of aluminum is present at 2%-20% v/v of the vaccine composition, more preferably between about 5% and about 17% v/v.

In certain embodiments, TXO-A adjuvants are prepared similarly to TXO adjuvants, and the source of aluminum is added to the aqueous solution.

In preparation of TCXO and TCXO-A adjuvants, cholesterol is dissolved in the oil solution, and the other steps of making TCXO and TCXO-A are similar to the steps used in preparation of TXO and TXO-A, respectively.

Antigens

The inventors have surprisingly discovered that the adjuvants of the instant invention are capable of causing sufficient protection from Foot-And-Mouth disease even when the dose of the antigen is decreased from 10 µg of the FMD virus to 0.5 µg. Thus, in different embodiments of the invention, the amount of the FMD virus may be 0.5 µg, about 1 µg, about 2 µg, about 3 µg, about 4 µg, about 5 µg, about 6 µg, about 7 µg, about 8 µg, about 9 µg or about 10 µg. The amount of the antigen may be between 0.5 and 1 µg, between 1 and 2 µg, between 2 and 3 µg, between 3 and 4 µg, between 4 and 5 µg, between 5 and 6 µg, between 6 and 8 µg, between 8 and 10 µg of FMD virus (140 S particles).

Currently, seven serotypes of FMD have been isolated. Of the seven serotypes of this virus, A, C, O, Asia 1, and SAT3 appear to be distinct lineages; SAT 1 and SAT 2 are unresolved clades. Within each serovar, multiple strains exist. For example, A24 Cruzeiro belongs to serotype A, and O1 Campos belongs to serotype O.

FMD virus of any serotype may be used as an antigen in this invention, provided that such virus is not pathogenic. Pathogenicity may be reduced by inactivation of the virus, e.g., treatment with formaldehyde or BEI.

In certain embodiments, the virus may be attenuated by culture passage or via recombinant means. It has previously been demonstrated, for example, that deletion of the leader protein L$^{pro}$ coding region results in FMD virus which is attenuated in cattle and pigs. See, e.g., U.S. Pat. Nos. 5,824,316, 8,765,141, Virology 1997 227(1): 96-102, J. Virol 2012 86:11675-11685. Point mutations in at positions 55 and 58 within the SAP domain of L protein also resulted in a viable virus that displayed a mild attenuated phenotype in cell culture and was protective in swine FMD model. See U.S. Pat. No. 8,846,057.

In certain embodiments, the virus also contains negative antigenic markers which allow for DIVA (differentiating infected from vaccinated animals) assays. In certain embodiments, the negative antigenic markers are introduced to 3D and/or 3B proteins. See, e.g., SEQ ID NOs 19, 20, 21, 22.

Like other viruses, the FMD virus continually evolves and mutates, thus one of the difficulties in vaccinating against it is the huge variation between, and even within, serotypes. There is no cross-protection between serotypes (a vaccine for one serotype will not necessarily protect against any others) and in addition, two strains within a given serotype may have nucleotide sequences that differ by as much as 30% for a given gene. This means FMD vaccines must be highly specific to the strain involved.

Thus, in certain embodiments, endonuclease restriction sites are introduced into the genome of the virus, thereby allowing introduction of proteins (e.g., proteins forming the outer capsids) from heterologous FMD strains.

In certain embodiments, the antigen component comprises FMD strain A24 Cruzeiro, which may optionally be modified by deletion of leader protein, negative marker mutations in 3B and/or 3D proteins, and by introduction of restriction endonuclease sites for an easier introduction of sequences for antigens (e.g., capsid proteins) from heterologous strains. Suitable non-limiting examples of the antigens are described in U.S. Pat. No. 8,765,141. DNA sequences corresponding to RNA genome of a genetically modified FMDV are also provided in SEQ ID NO: 15 ($A_{24}LL3D_{YR}$) and SEQ ID NO: 17 ($A_{24}LL3B_{PVKV}3D_{YR}$). Thus, a DNA sequence complementary to the DNA sequence set forth e.g., in SEQ ID NO: 15 is a template for, i.e. is complementary to or "encodes", the RNA genome of the FMDV virus (i.e., RNA that encodes the FMDV). In certain embodiments, the virus comprises capsid protein(s) of heterologous FMD strains (i.e., strains of FMD other than $A_{24}$ Cruzeiro, including without limitations, strains of lineages C, O, Asia 1, SAT3, SAT 1 and SAT 2, Turkey 06 and other strains of lineage A). Non limiting examples of such heterologous antigens are illustrated in SEQ ID NO: 23 (Asia1-$A_{24}LL3B_{PVKV}3D_{YR}$) and SEQ ID NO: 24 (A/Turkey/06-$A_{24}LL3B_{PVKV}3D_{YR}$). Additionally, O1 campos-$A_{24}LL3B_{PVKV}3D_{YR}$ (complete genome, also referred as O1campos), C3 Indaial-$A_{24}LL3B_{PVKV}3D_{YR}$ (complete genome), and capsid Argentina 2001 iso93 (capsid and 2A partial sequence) are provided in SEQ ID NOs 25, 26, and 27, respectively.

Variants of such antigens are also envisioned. The variants are at least 80% identical (e.g., 85% identical, 90% identical, 95% identical, 96% identical, 97% identical, 98% identical or 99% identical) to a reference sequence using one of the alignment programs described using standard parameters. Multiple alignment tools are available to determine sequence identity, including, without limitations, BLAST, CLUSTAL or PHILIP.

One of skill in the art will recognize that these values can be appropriately adjusted to determine corresponding identity of proteins encoded by two nucleotide sequences by taking into account codon degeneracy, amino acid similarity, reading frame positioning, and the like.

In certain embodiments, the variants encompass more than the specific exemplary nucleotide or amino acid sequences and include functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The polypeptides of the invention may also be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified activities of the parent FMD virus. The mutations that will be made in the DNA encoding the variant must not place the sequence out of reading frame and preferably will not create complementary regions that could produce secondary mRNA structure.

Methods of growing and purifying the antigens suitable for the instant invention are well known in the art and include, without limitations, hollow fiber filtration and PEG precipitation. These methods yield somewhat different antigenic compositions. For example, in PEG precipitation, the antigenic composition is depleted of non-structural proteins. In other methods, such as, for example, hollow fiber filtration, the antigenic composition contains both structural and non-structural FMD proteins. Accordingly, in some embodiments, the FMD antigen comprises structural proteins. In other embodiments, such as, for example, where the FMD antigen is prepared by hollow fiber filtration, the FMD antigen comprises both structural and non-structural proteins, particularly 3D protein.

Using current vaccine platforms, devoid of intrinsic antigenic markers to differentiate vaccinated from infected animals, removal of non-structural proteins is desirable as this remains desirable due to the fact that presence of antibodies to non-structural protein identifies infected animals. However in the context of the FMDLL3B3D platform, the presence of non-structural protein in the antigen preparation does not preclude differentiation between vaccinated and infected animals. It is in this context that the present formulation of antigen including non-structural proteins and adjuvant provide both protection against clinical disease at lower doses than purified antigen formulations and also prevent more effectively the establishment of persistent infections in ruminants.

Compositions

The compositions of the present invention can be formulated following accepted convention to include acceptable carriers for animals, including humans, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

The compositions of the present invention can further comprise one or more additional immunomodulatory components such as, e.g., an additional adjuvant or cytokine, among others. Non-limiting examples of such additional adjuvants that can be used in the vaccine of the present invention include the RIBI adjuvant system (Ribi Inc., Hamilton, Mont.), Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Other immunomodulatory agents that can be included in the vaccine include, e.g., one or more interleukins, interferons, or other known cytokines.

The routes of administration for the adjuvant compositions include parenteral, oral, oronasal, intranasal, intratracheal, topical, subcutaneous, intramuscular, transcutaneous, intradermal, intraperitoneal, intraocular, intravenous, and lingual administration. Any suitable device may be used to administer the compositions, including syringes, droppers, needleless injection devices, patches, and the like. The route and device selected for use will depend on the composition of the adjuvant, the antigen, and the subject, and are well known to the skilled artisan.

In view of high infectivity of FMD, measures which need to be taken to contain and/or eliminate FMD outbreak are controlled by regulatory authorities, such as, for example, national Ministries of Agriculture and sanctioned by international organizations such as the OIE (International Office of Epizootics). The measures which need to be undertaken in connection with the outbreak may include, without limitations, standstill of animal movements, effective controls on the movement of animal products, including milk, meat, hide, etc, stamping-out policy (slaughter of the animals in affected herd, and, where appropriate, those in other herds which have been exposed to infection by direct animal to animal contact, or by indirect contact with the pathogen). Often the animals in the neighboring herds are vaccinated followed by slaughter.

The inventors have surprisingly discovered that certain immunogenic compositions described herein prevent persistence, which is defined as the presence or shedding of FMD for longer than 28 days after the infection. In certain embodiments, such immunogenic compositions comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose.

In certain embodiments, antigen may be present in the amount equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention, therefore, also provides a method of reducing frequency of FMD persistence in a ruminant infected with FMD comprising administering to said ruminant prior to the infection the immunogenic compositions which comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD (Foot-and-Mouth Disease) antigen in the amount equivalent to at least 6 µg of FMD virus per dose.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

Administration of these immunogenic compositions to ruminants (e.g., cattle, sheep, camels, etc.) allows for the change in herd management practices. In certain embodiments, the vaccinated members of the herd are not slaughtered after a suspected contact with FMD virus.

In alternative (or additional) embodiments, the vaccinated animals are kept in quarantine for a shorter time. Thus, in certain embodiments, the animals suspected of coming in contact with FMD may be kept in quarantine for less than 30 days, e.g., 28 days, or 29 days.

Further, designation of an area as a containment zone means severe limitations of prohibition on movement of animals or animal products from the containment zone, generally, 30 days or more. Thus, in certain embodiments, the animals suspected of coming in contact with FMD may be moved from the containment zone within less than 30 days, e.g., 28 days or 29 days from the suspected contact with FMD.

In the embodiments where the antigen component entails a genetically engineered FMD antigen, e.g., as described above, it is possible to differentiate vaccinated from infected animals. Therefore, in additional embodiments, the herd management methods (or method of reducing frequency of FMD persistence in a ruminant infected with FMD).

In other words, the immunogenic compositions, in certain embodiments comprising an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose may be used for herd management wherein, upon suspected contact with FMD infection, the vaccinated members of said herd are not slaughtered; and/or quarantined for 0-30 days after the suspected contact and/or moved beyond the infected premises within 30 days of the suspected contact.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention will be further described in the following non-limiting examples.

EXAMPLES

Example 1. Preparation of Antigens

Two methods were used to prepare the antigens: Hollow Fiber Filtration and PEG precipitation.

PEG (poly-ethylene glycol) precipitation methods have been known in the art. Briefly, BHK-21 cells were infected with the FMD virus. Then (24-36 h later) the cells were lysed by freeze-thawing, and cell lysate was clarified of cell debris by low speed centrifugation (500×g). PEG was added (8% w/v) to the supernatant containing both structural and non-structural proteins. The mixture was incubated for 12-18 hr at 4° C. During this incubation, FMDV particles associate with the PEG. Antigen was recovered by centrifugation at 16,000×g and collection of the precipitate pellet containing PEG and virus. The supernatant, containing cellular and viral non-structural proteins was discarded. The pellet, to which the virus particles are bound, was then washed with small volumes of buffer to elute the FMDV particles from the PEG.

An additional method described herein is based on hollow-fiber concentration, of FMDV culture supernatants. The steps of this method consist of successive filtration arrangement to remove first the cell debris and large material from the cultures (BHK-21 cells infected with the FMD virus and lysed by freeze-thawing). The culture material was pumped successively through a 10 µm capsule filter, a 4.5 µm capsule filter, then finally through a 0.8 µm/0.2 µm filter. This filtrate was then concentrated using a hollow fiber ultrafiltration cartridge that allows particles smaller than 0.01 µm to flow through the membrane. FMDV particles and many non-structural proteins remain in the column circuit while liquid and smaller proteins go through the membrane into the waste. The column circuit was run until the concentrate reaches the desired volume, normally a ten-fold concentration.

FIG. 1 is a Western blot illustrating the difference in quality between the PEG precipitated and hollow fiber concentrated antigens. Hollow fiber concentrated antigen contains large amounts of structural and non structural proteins as illustrated in this FIGURE by western blot staining using an antibody specific for protein 3D, the largest FMDV non-structural proteins and antibody specific to capsid protein (structural protein). In contrast, PEG-precipitated antigens (lane 9) contained structural protein but did not contain detectable levels of 3D protein.

Example 2. Effects of FMD Vaccines Adjuvanted with TXO

Animals and Sample Collection

Six- to eight-month-old Holstein steers weighing 180-230 kg were used in this study. The animals were free of FMDV-reactive antibodies as determined by 3D ELISA test prior to vaccination as determined later from serum samples taken on Day 0. All 28 animals were commingled in one room in a BSL-3-Ag animal testing facility. The animals were fed complete ration pellets or alfalfa cubes, with water and salt blocks available ad libitum. Animals were acclimatized five days to the facilities prior to Day 0. Animals were previously treated with Bovi-Shield GOLD® 5, Micotil® 300, Liquamycin® LA-200® and Dectomax®. Groups of animals (n=4 each) with consecutive ear tag numbers were assigned to a treatment group.

No adverse events were documented following vaccination.

Serum separator blood tubes to obtain serum samples were collected at Days 0 (before vaccination), 4, 7, 14, 21 (before challenge), 24, 28, 31 and 42 from all animals. The serum samples were kept frozen until tested for the presence of neutralizing antibodies against FMDV in a serum neutralization assay (reported as the reciprocal of the last serum dilution to neutralize 100 TCIDs of homologous FMDV in 50% of the wells) or to study the anti-3Dpol response (by means of a competitive Enzyme-Linked Immunosorbent Assay).

As recommended by the OIE ("Manual of Diagnostic Tests and Vaccines for Terrestrial Animals"), challenge of vaccinated cattle for vaccine efficacy was by needle inoculation by the intradermal lingual (IDL) route. At 21 days post-vaccination, all vaccinated and naïve animals were inoculated IDL with 10,000 BTID$_{50}$ (50% bovine tongue infectious doses) of homologous FMDV A$_{24}$ Cruzeiro divided as 4 inoculations of 0.1 ml/each with 2,500 BTID$_{50}$/ 0.1 ml. All animals were followed for 10 days post-challenge to assess development of clinical disease as expressed by fever, nasal secretion, salivation, loss of appetite and/or lameness. Clinical evaluation for the presence of hoof vesicles was performed with sedation (xylazine given IM at 0.22 mg/kg so as to maintain sternal recumbency for the duration of the procedure) at day 21 (before inoculation) and days 24, 28 and 31. The sedative was reversed with tolazoline, IV, at a dose of 2 mg/kg.

Vaccines

Antigens were prepared as described in Example 1. Antigen stock solutions contained 5.51 µg/ml antigen prepared by hollow fiber filtertration (Prep A) or 10.26 µg/ml antigen prepared by PEG precipitation (Prep B).

The details of the immunogenic compositions administered to the animals are provided in Table 1. Each group contained four animals.

TABLE 1

Study Design

| Group | Antigen | Amount/5 ml | Adjuvant/5 ml | Volume injected, ml, IM |
|---|---|---|---|---|
| T01 | None | N/A | PBS (Neg control) | 5 |
| T02 | FMDV (Prep B)-PEG ppt. | 8 µg | Light Mineral oil-SPAN® 80 | 5 |
| T03 | FMDV (Prep B) PEG ppt. | 2 µg | TWEEN® 80 DEAE Dextran (100 mg); | 1.25 |
| T04 | FMDV (Prep B)-PEG ppt. | 0.5 µg | SEQ ID NO: 8; 75% pure: 100 µg | 0.3125 |
| T05 | FMDV (Prep A)-Hollow fiber filt.- | 8 µg | | 5 |
| T06 | FMDV (Prep A)-Hollow fiber filt. | 2 µg | | 1.25 |
| T07 | FMDV (Prep A)-Hollow fiber filt. | 0.5 µg | | 0.3125 |

The immunogenic compositions of groups T02 through T06 were homogenized on the day of vaccination and administered to the animals on Day 0.

Persistence was measured as the presence or absence of virus (either FMDV viral RNA and/or infectious FMDV) determined using both viral isolation and quantitative rRT-PCR. The primers used for the quantitative rRT-PCR were as follows:

```
Forward (SEQ ID NO: 28):
GACAAAGGTTTTGTTCTTGGTCA

Reverse (SEQ ID NO: 29):
TGCGAGTCCTGCCACGGA

Taqman probe: (FAM reporter, TAMRA quencher,
SEQ ID NO: 30)
TCCTTTGCACGCCGTGGGAC
```

Serum neutralizing titers to FMDV are summarized in Table 2.

TABLE 2

Serum Neutralizing Titers

| Treatment | Serum Neutralizing Titer | | |
|---|---|---|---|
| | Day 0 | Day 21 | Day 42 |
| T01 | 0.45 [a] | 0.45 [a] | 2.62 [ab] |
| T02 | 0.45 [a] | 1.64 [c] | 2.84 [b] |
| T03 | 0.45 [a] | 0.90 [b] | 2.39 [ab] |
| T04 | 0.45 [a] | 0.76 [b] | 2.74 [ab] |
| T05 | 0.45 [a] | 1.55 [c] | 2.28 [a] |

TABLE 2-continued

Serum Neutralizing Titers

| Treatment | Serum Neutralizing Titer | | |
|---|---|---|---|
| | Day 0 | Day 21 | Day 42 |
| T06 | 0.45 [a] | 0.81 [b] | 2.36 [ab] |
| T07 | 0.45 [a] | 0.54 [a] | 2.68 [ab] |

[a,b,c] Treatment groups with same letter within each day are not significantly different at alpha = 0.05

Signs of FMDV were scored as presence (1) or absence (0) of hoof vesicles, i.e., a presence of a vesicle on a single hoof produced the score of 1, the presence of vesicles on only 2 hooves produced score of 2 and vesicles on all 4 hooves produced a score of 4. Once an animal received a score of 4, it was considered to have a score of 4 for the duration of the study.

The scores from individual animals for each hoof and for each day of examination are shown in Table 3. In Table 4, a summary of each animal's scores according to whether any hoof was positive is presented.

TABLE 3

FMDV Vesicle Scoring individual Animal Listing

| | | Day of Study | | | | | | | |
|---|---|---|---|---|---|---|---|---|---|
| | | 21 | | | | 24 | | | |
| | | Location | | | | Location | | | |
| Treatment | Animal | LEFT FORE | LEFT REAR | RIGHT FORE | RIGHT REAR | LEFT FORE | LEFT REAR | RIGHT FORE | RIGHT REAR |
| T01 | R14-84 | 0 | 0 | 0 | 0 | 0 | 1 | 0 | 1 |
| | R14-85 | 0 | 0 | 0 | 0 | 1 | 1 | 1 | 1 |
| | R14-86 | 0 | 0 | 0 | 0 | 0 | 1 | 0 | 0 |
| | R14-87 | 0 | 0 | 0 | 0 | 1 | 1 | 1 | 1 |
| T02 | R14-72 | 0 | 0 | 0 | 0 | 0 | 0 | 0 | 0 |
| | R14-73 | 0 | 0 | 0 | 0 | 0 | 0 | 0 | 0 |
| | R14-74 | 0 | 0 | 0 | 0 | 0 | 0 | 0 | 0 |
| | R14-75 | 0 | 0 | 0 | 0 | 0 | 0 | 0 | 0 |
| T03 | R14-76 | 0 | 0 | 0 | 0 | 0 | 0 | 0 | 0 |
| | R14-77 | 0 | 0 | 0 | 0 | 0 | 1 | 0 | 0 |
| | R14-78 | 0 | 0 | 0 | 0 | 0 | 0 | 0 | 0 |
| | R14-79 | 0 | 0 | 0 | 0 | 0 | 0 | 0 | 0 |
| T04 | R14-80 | 0 | 0 | 0 | 0 | 0 | 0 | 0 | 0 |
| | R14-81 | 0 | 0 | 0 | 0 | 0 | 0 | 0 | 0 |
| | R14-82 | 0 | 0 | 0 | 0 | 0 | 0 | 0 | 0 |
| | R14-83 | 0 | 0 | 0 | 0 | 0 | 0 | 0 | 0 |
| T05 | R14-60 | 0 | 0 | 0 | 0 | 0 | 0 | 0 | 0 |
| | R14-61 | 0 | 0 | 0 | 0 | 0 | 0 | 0 | 0 |
| | R14-62 | 0 | 0 | 0 | 0 | 0 | 0 | 0 | 0 |
| | R14-63 | 0 | 0 | 0 | 0 | 0 | 0 | 0 | 0 |
| T06 | R14-64 | 0 | 0 | 0 | 0 | 0 | 0 | 0 | 0 |

TABLE 3-continued

FMDV Vesicle Scoring individual Animal Listing

|  |  |  |  |  |  |  |  |  |  |
|---|---|---|---|---|---|---|---|---|---|
|  | R14-65 | 0 | 0 | 0 | 0 | 0 | 0 | 0 | 0 |
|  | R14-66 | 0 | 0 | 0 | 0 | 0 | 0 | 0 | 0 |
|  | R14-67 | 0 | 0 | 0 | 0 | 0 | 0 | 0 | 0 |
| T07 | R14-68 | 0 | 0 | 0 | 0 | 0 | 0 | 0 | 0 |
|  | R14-69 | 0 | 0 | 0 | 0 | 0 | 0 | 0 | 0 |
|  | R14-70 | 0 | 0 | 0 | 0 | 0 | 0 | 0 | 0 |
|  | R14-71 | 0 | 0 | 0 | 0 | 0 | 0 | 0 | 0 |

| | | Day of Study | | | | | | | |
|---|---|---|---|---|---|---|---|---|---|
| | | 28 Location | | | | 31 Location | | | |
| Treatment | Animal | LEFT FORE | LEFT REAR | RIGHT FORE | RIGHT REAR | LEFT FORE | LEFT REAR | RIGHT FORE | RIGHT REAR |
| T01 | R14-84 | 1 | 1 | 1 | 1 | 1* | 1* | 1* | 1* |
|  | R14-85 | 1* | 1* | 1* | 1* | 1* | 1* | 1* | 1* |
|  | R14-86 | 1 | 1 | 1 | 1 | 1* | 1* | 1* | 1* |
|  | R14-87 | 1* | 1* | 1* | 1* | 1* | 1* | 1* | 1* |
| T02 | R14-72 | 0 | 0 | 0 | 0 | 0 | 0 | 0 | 0 |
|  | R14-73 | 0 | 0 | 0 | 0 | 0 | 0 | 0 | 0 |
|  | R14-74 | 0 | 0 | 0 | 0 | 0 | 0 | 0 | 0 |
|  | R14-75 | 0 | 0 | 0 | 0 | 0 | 0 | 0 | 0 |
| T03 | R14-76 | 0 | 0 | 0 | 0 | 0 | 0 | 0 | 0 |
|  | R14-77 | 0 | 1 | 0 | 0 | 0 | 1 | 0 | 0 |
|  | R14-78 | 0 | 0 | 0 | 0 | 0 | 0 | 0 | 0 |
|  | R14-79 | 0 | 0 | 0 | 0 | 0 | 0 | 0 | 0 |
| T04 | R14-80 | 0 | 0 | 0 | 0 | 0 | 0 | 0 | 0 |
|  | R14-81 | 0 | 0 | 0 | 0 | 0 | 0 | 0 | 0 |
|  | R14-82 | 0 | 0 | 0 | 0 | 0 | 0 | 0 | 0 |
|  | R14-83 | 0 | 0 | 0 | 0 | 0 | 0 | 0 | 0 |
| T05 | R14-60 | 0 | 0 | 0 | 0 | 0 | 0 | 0 | 0 |
|  | R14-61 | 0 | 0 | 0 | 0 | 0 | 0 | 0 | 0 |
|  | R14-62 | 0 | 0 | 0 | 0 | 0 | 0 | 0 | 0 |
|  | R14-63 | 0 | 0 | 0 | 0 | 0 | 0 | 0 | 0 |
| T06 | R14-64 | 0 | 0 | 0 | 0 | 0 | 0 | 0 | 0 |
|  | R14-65 | 0 | 0 | 0 | 0 | 0 | 0 | 0 | 0 |
|  | R14-66 | 0 | 0 | 0 | 0 | 0 | 0 | 0 | 0 |
|  | R14-67 | 0 | 0 | 0 | 0 | 0 | 0 | 0 | 0 |

TABLE 3-continued

FMDV Vesicle Scoring individual Animal Listing

| T07 | R14-68 | 0 | 0 | 0 | 0 | 0 | 0 | 0 | 0 |
| --- | --- | --- | --- | --- | --- | --- | --- | --- | --- |
| | R14-69 | 0 | 0 | 0 | 0 | 0 | 0 | 0 | 0 |
| | R14-70 | 0 | 0 | 0 | 0 | 0 | 0 | 0 | 0 |
| | R14-71 | 0 | 0 | 0 | 0 | 0 | 0 | 0 | 0 |

*Automatically scored as a '1' since all hooves for this animal previously had vesicles on all four hooves.

TABLE 4

FMDV Vesicle Scoring-Any Hoof Location Positive

| | | Day of Study | | | |
| --- | --- | --- | --- | --- | --- |
| Treatment | Animal | 21 | 24 | 28 | 31 |
| T01 | R14-84 | No | Yes | Yes | Yes* |
| | R14-85 | No | Yes | Yes* | Yes* |
| | R14-86 | No | Yes | Yes | Yes* |
| | R14-87 | No | Yes | Yes* | Yes* |
| T02 | R14-72 | No | No | No | No |
| | R14-73 | No | No | No | No |
| | R14-74 | No | No | No | No |
| | R14-75 | No | No | No | No |
| T03 | R14-76 | No | No | No | No |
| | R14-77 | No | Yes | Yes | Yes |
| | R14-78 | No | No | No | No |
| | R14-79 | No | No | No | No |
| T04 | R14-80 | No | No | No | No |
| | R14-81 | No | No | No | No |
| | R14-82 | No | No | No | No |
| | R14-83 | No | No | No | No |
| T05 | R14-60 | No | No | No | No |
| | R14-61 | No | No | No | No |
| | R14-62 | No | No | No | No |
| | R14-63 | No | No | No | No |
| T06 | R14-64 | No | No | No | No |
| | R14-65 | No | No | No | No |
| | R14-66 | No | No | No | No |
| | R14-67 | No | No | No | No |
| T07 | R14-68 | No | No | No | No |
| | R14-69 | No | No | No | No |
| | R14-70 | No | No | No | No |
| | R14-71 | No | No | No | No |

*Automatically scored as Yes since all hooves for this animal previously had vesicles on all four hooves All animals in T01 (negative control) exhibited hoof vesicles starting on Day 24. On Days 28 and 31, all hooves in all T01 animals were found to have vesicles. In contrast, full protection (i.e., no hoof vesicles) was observed for every group except T03 (2 μg dose of FMDV precipitated with PEG), where one animal (R14-77) received the score of 1 at Days 24, 28, and 31. The effects of the tested immunogenic compositions on persistent infection are illustrated in Tables 5 and 6. Persistence was defined as presence of infectious virus or viral RNA in oesophageal-pharyngeal fluid (obtained using a "Probang" cup) after 28 days post-challenge (day 49 after vaccination, as shown in tables 5 and 6). In Table 5, quantitative rRT-PCR results for individual animals and treatment group back-transformed least square means of FMDV RNA copy numbers per mL from probang samples are shown. In Table 6, results of probang sample virus isolation testing are reported as either positive or negative. The values below 1.87 in table 5 were scored as 'negative' due to limit of detection of the assay.

TABLE 5

Probang rRT-PCR Individual Animal Listing and Back-Transformed Least Squares Means per Treatment Group

| Treatment Number | Animal | Day 38 Test Result | Day 42 Test Result | Day 49 Test Result | Day 52 Test Result |
| --- | --- | --- | --- | --- | --- |
| T01 | R14-84 | 4.29 | 4.72 | <1.87 | 3.83 |
| T01 | R14-85 | 4.26 | 6.01 | 5.14 | 4.7 |
| T01 | R14-86 | <1.87 | 3.62 | <1.87 | <1.87 |
| T01 | R14-87 | <1.87 | <1.87 | <1.87 | <1.87 |
| Group Mean | | 1.999 | 3.130 | 1.432 | 1.992 |
| T02 | R14-72 | <1.87 | <1.87 | <1.87 | <1.87 |
| T02 | R14-73 | <1.87 | <1.87 | <1.87 | <1.87 |
| T02 | R14-74 | <1.87 | <1.87 | <1.87 | <1.87 |
| T02 | R14-75 | <1.87 | <1.87 | <1.87 | <1.87 |
| Group Mean | | 0.935 | 0.935 | 0.935 | 0.935 |
| T03 | R14-76 | 4.98 | 4.68 | <1.87 | <1.87 |
| T03 | R14-77 | 5.52 | 3.43 | <1.87 | <1.87 |
| T03 | R14-78 | <1.87 | 4.35 | <1.87 | 5.3 |
| T03 | R14-79 | <1.87 | <1.87 | <1.87 | <1.87 |
| Group Mean | | 2.214 | 2.843 | 0.935 | 1.443 |
| T04 | R14-80 | <1.87 | <1.87 | 4.88 | 4.59 |
| T04 | R14-81 | 5.08 | 4.01 | 3.98 | 4.65 |
| T04 | R14-82 | <1.87 | 4.47 | 6.12 | 4.32 |
| T04 | R14-83 | <1.87 | <1.87 | <1.87 | <1.87 |
| Group Mean | | 1.427 | 1.990 | 3.247 | 3.047 |
| T05 | R14-60 | <1.87 | <1.87 | <1.87 | <1.87 |
| T05 | R14-61 | <1.87 | <1.87 | <1.87 | <1.87 |
| T05 | R14-62 | 4.75 | <1.87 | <1.87 | <1.87 |
| T05 | R14-63 | <1.87 | <1.87 | <1.87 | <1.87 |
| Group Mean | | 1.404 | 0.935 | 0.935 | 0.935 |
| T06 | R14-64 | <1.87 | <1.87 | <1.87 | <1.87 |
| T06 | R14-65 | 4.10 | 4.11 | <1.87 | 3.39 |
| T06 | R14-66 | <1.87 | <1.87 | <1.87 | <1.87 |
| T06 | R14-67 | 4.14 | 5.08 | 5.18 | 4.82 |
| Group Mean | | 1.963 | 2.067 | 1.434 | 1.944 |
| T07 | R14-68 | <1.87 | <1.87 | <1.87 | <1.87 |
| T07 | R14-69 | <1.87 | <1.87 | <1.87 | <1.87 |
| T07 | R14-70 | <1.87 | <1.87 | <1.87 | <1.87 |
| T07 | R14-71 | 5.34 | 5.46 | 4.49 | 3.7 |
| Group Mean | | 1.445 | 1.453 | 1.384 | 1.319 |

TABLE 6

Probang Sample Virus Isolation - Individual Animal Listing

| | | Day of Study | | | |
| --- | --- | --- | --- | --- | --- |
| Treatment | Animal | 38 | 42 | 49 | 52 |
| T01 | R14-84 | Pos | Pos | Pos | Pos |
| | R14-85 | Pos | Pos | Pos | Pos |
| | R14-86 | Neg | Neg | Neg | Neg |
| | R14-87 | Neg | Neg | Neg | Neg |
| T02 | R14-72 | Neg | Neg | Neg | Neg |
| | R14-73 | Neg | Neg | Neg | Neg |
| | R14-74 | Neg | Pos | Neg | Neg |
| | R14-75 | Neg | Neg | Neg | Neg |

TABLE 6-continued

Probang Sample Virus Isolation - Individual Animal Listing

| Treatment | Animal | Day of Study | | | |
|---|---|---|---|---|---|
| | | 38 | 42 | 49 | 52 |
| T03 | R14-76 | Pos | Pos | Neg | Pos |
| | R14-77 | Pos | Pos | Neg | Neg |
| | R14-78 | Pos | Pos | Pos | Pos |
| | R14-79 | Neg | Neg | Neg | Neg |
| T04 | R14-80 | Pos | Neg | Pos | Pos |
| | R14-81 | Pos | Pos | Pos | Pos |
| | R14-82 | Pos | Pos | Pos | Pos |
| | R14-83 | Pos | Pos | Pos | Pos |
| T05 | R14-60 | Neg | Neg | Neg | Neg |
| | R14-61 | Neg | Neg | Neg | Neg |
| | R14-62 | Neg | Neg | Neg | Neg |
| | R14-63 | Neg | Neg | Neg | Neg |
| T06 | R14-64 | Neg | Neg | Neg | Neg |
| | R14-65 | Pos | Pos | Pos | Pos |
| | R14-66 | Neg | Neg | Neg | Neg |
| | R14-67 | Pos | Pos | Pos | Pos |
| T07 | R14-68 | Neg | Neg | Neg | Neg |
| | R14-69 | Neg | Neg | Neg | Neg |
| | R14-70 | Neg | Neg | Neg | Neg |
| | R14-71 | Pos | Pos | Pos | Pos |

For Group 1 (saline control), three animals were positive at least once for FMDV by rRT-PCR and two animals were always positive for virus isolation.

In Group T02, no animal was ever found to be carrying FMDV by rRT-PCR, but one animal (R14-74) was found to be positive by virus isolation assay at a single time point only (Day 42: day 21 post-challenge) but negative thereafter (Days 49:and 52, indicating the absence of persistent infection. The other animals in T02 did not carry FMDV detectable either by rRT-PCR or by viral isolation assay at day 38 and beyond.

In group T03, one animal (R14-79) was fully protected from FMDV infection, two animals demonstrated the presence of FMDV (either by rRT-PCR or by viral isolation assay) on three or four of the testing days and one animal (R14-77) demonstrated FMDV presence by both tests on Days 38 and 42, but not thereafter.

In group T04, all four animals exhibited persistence of FMDV by one or both tests through Day 52.

In Group T05, one animal (R14-62) demonstrated the presence of the virus only on Day 38 by rRT-PCR but not by virus isolation and and virus was not detected by either test thereafter. FMDV was not detected either by rRT-PCR or by viral isolation assay at any time for the other three animals in group T05.

In Group T06, two animals were fully protected from persistence while the other two were either rRT-PCR or virus isolation positive at every time point examined.

In group T07, three out of four animals were fully protected while one animal (R14-71) was positive for both rRT-PCR and virus isolation at each time point.

Table 7 summarizes the results of persistence experiments. Animals were considered as non-persistent if neitherrRT-PCR or viral isolation assays detected FMDV on both day 49 (28 days post-challenge) and day 52 (31 day post-challenge).

TABLE 7

| Frequency of Persistence and Non-Persistence | | |
|---|---|---|
| Treatment | Persistent % | Not Persistent % |
| T01 (saline) | 50 | 50 |
| T02 (FMDV PEG ppt-8 μg) | 0 | 100 |
| T03 (FMDV PEG ppt-2 μg) | 50 | 50 |
| T04 (FMDV PEG ppt-0.5 μg) | 100 | 0 |
| T05 (FMDV Hollow fiber-8 μg) | 0 | 100 |
| T06 (FMDV Hollow fiber-2 μg) | 50 | 50 |
| T07 (FMDV Hollow fiber-0.5 μg) | 25 | 75 |

Only two of the eight animals administered 8 μg of antigen (Groups T02 and T05) ever exhibited the presence of virus and that was for one day only (one each on Days 37 and 42). The other animals in these groups were fully protected Considering that the virus presence was not detected on both 28 and 31 days after infection, none of the animals administered 8 μg of antigen was considered to be persistently infected. Five out of eight animals administered 2 μg of antigen (Groups T03 and T06) exhibited viral persistence. Four out of eight animals eight animals administered 0.5 μg of antigen (Groups T04 and T07) exhibited persistence.

Taken together, these results indicate protection from FMDV viral persistence in animals administered 8 μg antigen, and it also appears that the purification of the antigen by hollow fiber filtration is advantageous compared to PEG precipitation. The main difference between the two antigen formulations is the presence of non-structural proteins in addition to structural ones in the hollow fiber filtration formulation. Thus, without being bound by theory, it appears that the quality of the immune response elicited by vaccines where the antigen contains both structural and non-structural proteins, and particularly protein 3D, are more effective in preventive FMDV persistence, as illustrated in Table 8.

TABLE 8

| Effect of antigen preparation method on immune response. | | |
|---|---|---|
| Treatment | Persistent % | Not Persistent % |
| T01 (saline) | 50% (2 out of 4) | 50% (2 out of 4) |
| Prep A (hollow fiber, groups T05-T07 Combined) | 25% (3 out of 12) | 75% (9 out of 12) |
| Prep B (PEG precipitation, groups, T02-T04 Combined) | 50% (6 out of 12) | 50% (6 out of 12) |

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method of herd management, comprising administering to each member in said herd an immunogenic composition wherein said immunogenic composition comprises: a) antigen component comprising at least 6 µg of FMD (Foot-and-Mouth Disease) virus per dose; b) an emulsion containing an oil; c) 75-200 µg of a CpG-containing immunostimulatory oligonucleotide per dose; d) 75-200 mg of a polycationic carrier per dose, and wherein further, upon suspected contact with FMD infection, the vaccinated members of said herd are not slaughtered and wherein the CpG containing immunostimulatory oligonucleotide comprises a 5' TLR activation domain and at least two palindromic regions, one palindromic region being a 5' palindromic region of at least 6 nucleotides in length and connected to a 3' palindromic region of at least 8 nucleotides in length either directly or through a spacer.

2. A method of herd management, comprising administering to each member in said herd an immunogenic composition wherein said immunogenic composition comprises: a) antigen component comprising at least 6 µg of FMD (Foot-and-Mouth Disease) virus per dose; b) an emulsion containing an oil; c) 75-200 µg of a CpG-containing immunostimulatory oligonucleotide per dose; d) 75-200 mg of a polycationic carrier per dose, and wherein further, upon suspected contact with FMD infection, the vaccinated members of said herd are quarantined for 0-30 days.

3. A method of herd management, comprising administering to each member in said herd an immunogenic composition wherein said immunogenic composition comprises: a) antigen component comprising at least 6 µg of FMD (Foot-and-Mouth Disease) virus per dose; b) an emulsion containing an oil; c) 75-200 µg of a CpG-containing immunostimulatory oligonucleotide per dose; d) 75-200 mg of a polycationic carrier per dose, and wherein further, upon suspected contact with FMD infection, the vaccinated members of said herd are moved beyond the infected premises.

4. The method according to claim 1, wherein the vaccinated members of the herd are not slaughtered and are quarantined for 0-30 days.

5. The method according to any one of claims 1-4, wherein CpG containing immunostimulatory oligonucleotide comprises at least one of:
a) an iodo-modified nucleotide;
b) one or more phosphorothioate bonds.

6. The method according to claim 5, wherein the iodo-modified nucleotide is the 5'-nucleotide of said CpG containing immunostimulatory oligonucleotide.

7. The method according to claim 6, wherein the immunostimulatory oligonucleotide comprises one or more phosphorothioate bonds and an iodo-modified nucleotide.

8. The method according to claim 7, wherein the polycationic polymer is diethylaminoethyl (DEAE) Dextran.

9. The method according to claim 8, wherein the oil is a light mineral oil.

10. The method according to claim 9, wherein oily phase comprises 50.01%-55% v/v of the immunogenic composition.

11. The method of claim 10, wherein said immunogenic composition comprises 6-20 µg of FMD (Foot-and-Mouth Disease) virus per dose.

12. The method of claim 10, wherein said immunogenic composition comprises 6-18 µg of FMD (Foot-and-Mouth Disease) virus per dose.

13. The method of claim 10, wherein said immunogenic composition comprises 8-12 µg of FMD (Foot-and-Mouth Disease) virus per dose.

* * * * *